United States Patent
Nishio et al.

(10) Patent No.: US 8,439,899 B2
(45) Date of Patent: May 14, 2013

(54) REMOTE-CONTROLLED ACTUATOR

(75) Inventors: Yukihiro Nishio, Shizuoka (JP); Hiroshi Isobe, Shizuoka (JP); Yoshitaka Nagano, Shizuoka (JP)

(73) Assignee: NTN Corporation, Osaka (JP)

( * ) Notice: Subject to any disclaimer, the term of this patent is extended or adjusted under 35 U.S.C. 154(b) by 203 days.

(21) Appl. No.: 13/062,711

(22) PCT Filed: Sep. 10, 2009

(86) PCT No.: PCT/JP2009/004481
§ 371 (c)(1),
(2), (4) Date: Mar. 8, 2011

(87) PCT Pub. No.: WO2010/029741
PCT Pub. Date: Mar. 18, 2010

(65) Prior Publication Data
US 2011/0203825 A1    Aug. 25, 2011

(30) Foreign Application Priority Data

Sep. 11, 2008  (JP) .................................. 2008-233001
Nov. 19, 2008  (JP) .................................. 2008-295181

(51) Int. Cl.
*A61B 17/16* (2006.01)
(52) U.S. Cl.
USPC ............................................. 606/1; 74/469
(58) Field of Classification Search .............. 74/39, 213; 173/422, 519, 469; 606/1
See application file for complete search history.

(56) References Cited

U.S. PATENT DOCUMENTS

| | | | |
|---|---|---|---|
| 4,265,231 A | 5/1981 | Scheller, Jr. et al. | |
| 4,466,429 A | 8/1984 | Loscher et al. | |
| 5,356,064 A | 10/1994 | Green et al. | |
| 5,662,666 A | 9/1997 | Onuki et al. | |
| 7,204,844 B2* | 4/2007 | Jensen et al. | 606/205 |
| 7,717,653 B2 | 5/2010 | Miyata et al. | |
| 8,123,740 B2* | 2/2012 | Madhani et al. | 606/1 |
| 2002/0111635 A1* | 8/2002 | Jensen et al. | 606/130 |
| 2005/0150123 A1* | 7/2005 | Eaton | 33/503 |
| 2005/0192595 A1* | 9/2005 | Green et al. | 606/130 |
| 2005/0273086 A1* | 12/2005 | Green et al. | 606/1 |

(Continued)

FOREIGN PATENT DOCUMENTS

| | | |
|---|---|---|
| JP | 06-315486 A | 11/1994 |
| JP | 09-135837 A | 5/1997 |

(Continued)

*Primary Examiner* — Henry M Johnson, III
(74) *Attorney, Agent, or Firm* — Pierce Atwood LLP; Kevin M. Farrell; Katherine A. Wrobel

(57) ABSTRACT

A remote controlled actuator includes an elongated spindle guide section and a distal end member fitted to a distal end thereof for alteration in attitude. The distal end member rotatably supports a spindle for holding a tool. The spindle guide section includes a rotary shaft for transmitting rotation of a tool rotation drive source to the spindle. An attitude altering member inserted in a guide hole is selectively advanced or retracted by an attitude control drive source. An initial attitude hold control unit controls the attitude control drive source so that an initial attitude holding force necessary to maintain the distal end member in the initial attitude can be applied to the attitude altering member. An attitude alteration control unit controls the attitude control drive source so that the attitude of the distal end member can be altered by a force larger than the initial attitude holding force.

8 Claims, 13 Drawing Sheets

U.S. PATENT DOCUMENTS

| | | | |
|---|---|---|---|
| 2007/0213692 A1* | 9/2007 | Neubauer et al. | 606/1 |
| 2007/0258782 A1 | 11/2007 | Miyata et al. | |
| 2007/0265653 A1 | 11/2007 | Suzuki | |
| 2010/0057087 A1* | 3/2010 | Cha | 606/80 |
| 2011/0138962 A1* | 6/2011 | Ozaki et al. | 74/519 |
| 2011/0213347 A1* | 9/2011 | Lee et al. | 606/1 |
| 2011/0230868 A1* | 9/2011 | Isobe et al. | 606/1 |

FOREIGN PATENT DOCUMENTS

| | | |
|---|---|---|
| JP | 2001-17446 A | 1/2001 |
| JP | 2005-528159 A | 9/2005 |
| JP | 2007-301149 A | 11/2007 |
| JP | 2007-301641 A | 11/2007 |
| WO | 03/101308 A1 | 12/2003 |

* cited by examiner

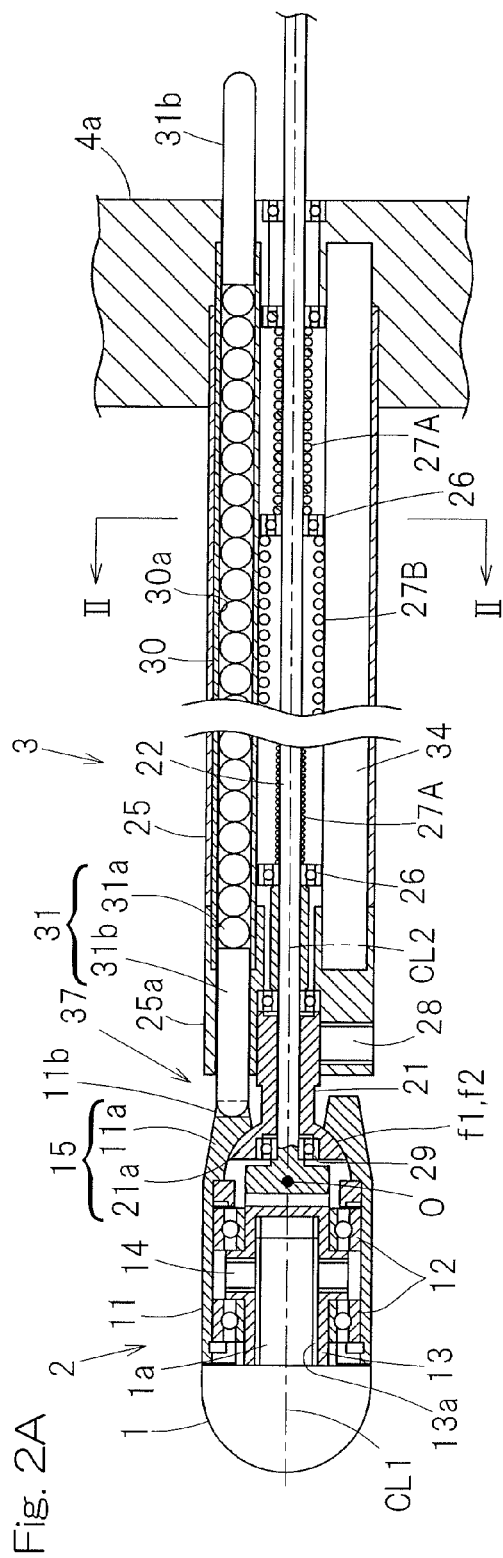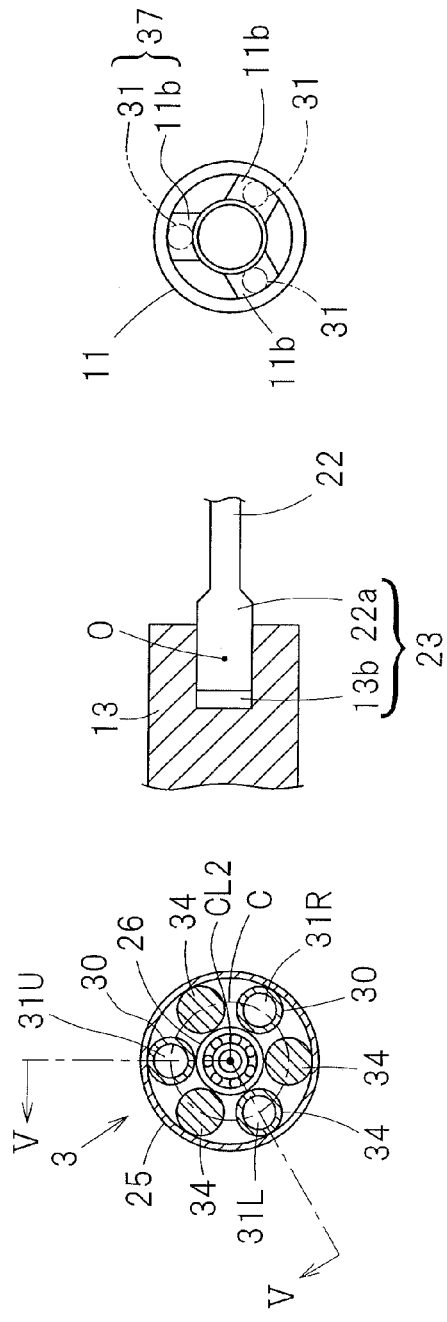

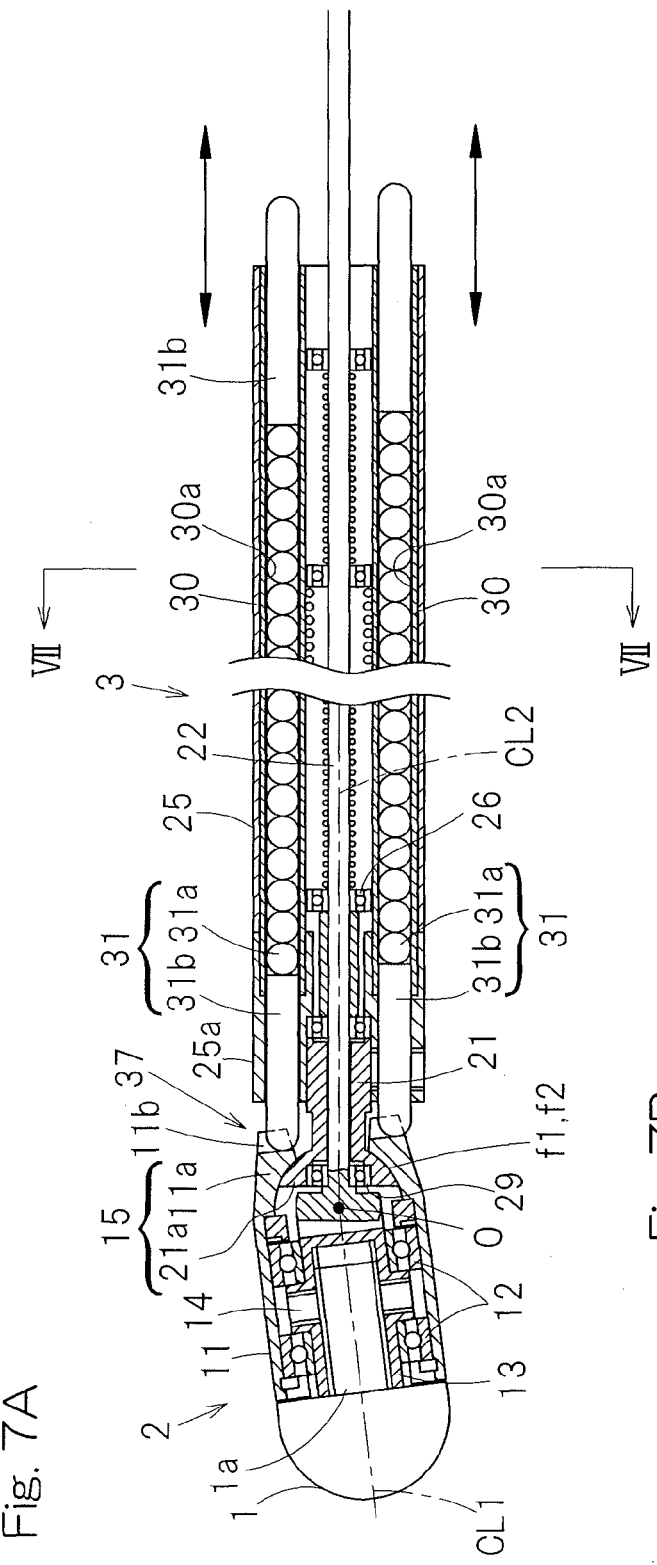
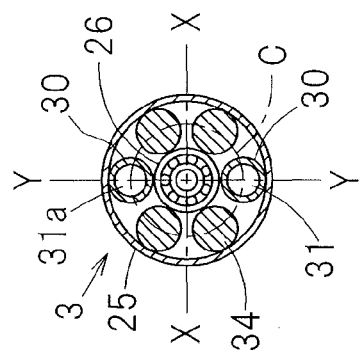
Fig. 7A
Fig. 7B

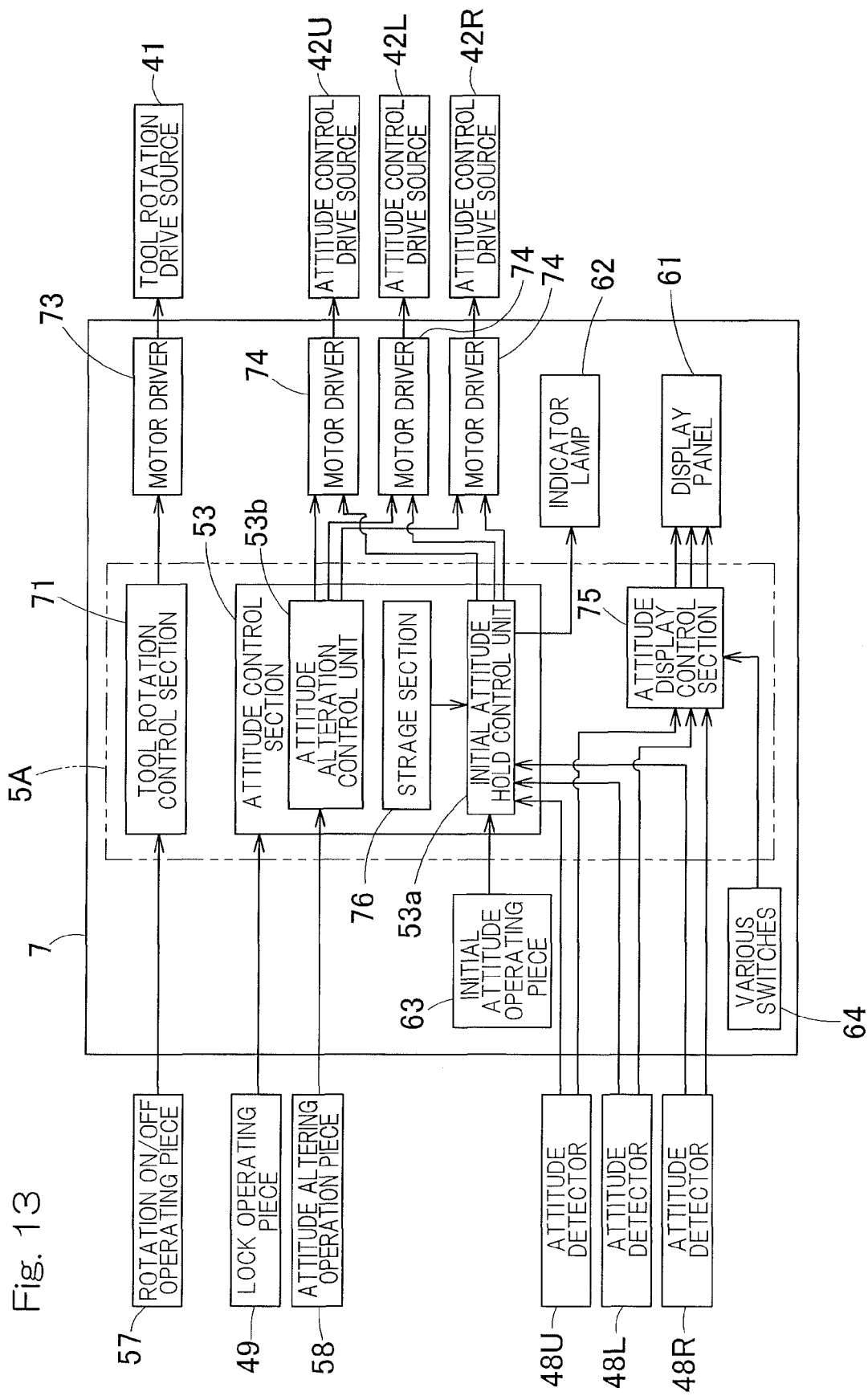

REMOTE-CONTROLLED ACTUATOR

CROSS REFERENCE TO THE RELATED APPLICATION

This application is based on and claims Convention priority to Japanese patent applications No. 2008-233001, filed Sep. 11, 2008, and No. 2008-295181, filed Nov. 19, 2008, the entire disclosures of which are herein incorporated by reference as a part of this application.

BACKGROUND OF THE INVENTION

1. Field of the Invention

The present invention relates to a remote controlled actuator for use in medical and machine processing fields and capable of changing the attitude of a machine tool.

2. Description of Related Art

Remote controlled actuators are currently available; some are used in the medical field for osteal treatment and some are used in the mechanical processing field for drilling and cutting a bone. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded due to bone deterioration, is replaced with an artificial joint. The joint replacement surgery requires a living bone of a patient to be processed to enable an artificial joint to be implanted, but in order to enhance the strength of postoperative adhesion between the living bone and the artificial joint, such processing is required to be performed precisely and accurately in conformity to the shape of the artificial joint.

By way of example, during the hip join replacement surgery, a thigh bone is opened to secure access of an artificial joint into the femoral marrow cavity. In order to secure a strength of contact between the artificial joint and the bone, surfaces of contact between the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular incision. In other words, the human body must be invaded. In order to minimize the postoperative trace, it is quite often desirable that the elongated pipe referred to above is not necessarily straight, but is moderately curved. To meet with this desire, the following technique has hitherto been suggested. For example, Patent Document 2 listed below discloses the elongated pipe having its intermediate portion curved double to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, Patent Document 3 listed below discloses the elongated pipe rotated 180°.

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-17446

If in a condition, in which the artificial joint is inserted into an artificial joint insertion hole formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever the pipe take any shape, the working range of the tool is limited by the shape of the pipe and, therefore, it is difficult to widen the working range of the tool to process the artificial joint insertion hole so that the living bone and the artificial joint may can have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant of the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It is noted that in the case of the medical actuator having no elongated pipe used therein, a portion where the tool is mounted can change its attitude relative to a portion to be gripped by hand (See, for example, Patent Document 4 listed above.), but nothing has yet been suggested in the art that the attitude of the tool can be changed by remote control.

SUMMARY OF THE INVENTION

An object of the present invention is to provide a remote controlled actuator of a type, in which the attitude of the tool coupled to the distal end of the elongated pipe can be changed by remote control and in which the attitude of the tool can be properly maintained not only during the initial attitude persistence, but also during the attitude changing time.

The remote controlled actuator according to the present invention includes a spindle guide section of an elongated shape, a distal end member fitted to a distal end of the spindle guide section through a distal end member coupling unit for alteration in attitude, and a drive unit housing coupled with a base end of the spindle guide section. The distal end member rotatably supports a spindle for holding a tool. The spindle guide section includes a rotary shaft for transmitting rotation of a tool rotation drive source, provided within the drive unit housing, to the spindle and a guide hole defined therein so as to extend from one end to the opposite end. An attitude altering or operating member having a tip end held in contact with the distal end member is reciprocally movably inserted within the guide hole. An attitude control drive source for applying to the attitude altering member a force acting in a direction of advance and retraction is provided within the drive source housing and, also, an attitude control section for controlling the attitude control drive source is provided. The attitude control section includes an initial attitude hold control unit for controlling the attitude control drive source to apply to the attitude altering member an initial attitude holding force necessary to enable the attitude of the distal end member to hold in an arbitrarily preset initial attitude, and an attitude alteration control unit for controlling the attitude control drive source to apply to the attitude altering member a force greater than the initial attitude holding force being applied to the attitude altering member so that the attitude of the distal end member is altered by selectively advancing or retracting the attitude altering member. In this remote controlled actuator, the initial attitude hold control unit controls the attitude control drive source so as to apply an initial attitude holding force, required to enable the attitude to be maintained in the arbitrarily preset initial attitude, to the attitude altering member.

According to the above described construction, the rotation of the tool rotation drive source is transmitted to the spindle of the distal end member through the rotary shaft so that the tool held by the spindle can be rotated to perform cutting of the bone or the like. At this time, the attitude of the distal end member is determined by the balance of the external force, acting on the distal end member, and the thrust force of the attitude control drive source. Accordingly, in the event that no force necessary to alter the attitude is applied by controlling the attitude control drive source so as to apply the initial attitude holding force to the attitude altering member, the distal end member is maintained in the initial attitude by means of the initial attitude hold control unit of the attitude control section due to the rigidity of the distal end member which rigidity then causes the distal end member to resume the arbitrarily preset initial attitude. By the effect of the thrust force of the attitude control drive source, the attitude of the distal end member is maintained, that is, securement of the rigidity of the distal member is achieved. Also, in the event that the large force never experienced with acts on the distal end member when, for example, the attitude of the distal end member is to be altered, it is necessary to increase the thrust force of the attitude control drive source in order to maintain the attitude of the distal end member. In view of this, when the attitude of the distal end member is desired to be altered, the attitude control drive source is controlled so that the force larger than the initial attitude holding force can be applied by the attitude alteration control unit of the attitude control section to the attitude altering member. In this way, since the attitude of the distal member at the time of the initial attitude is controlled by the initial attitude hold control unit and the attitude of the distal end member at the time of alteration of the attitude is controlled by the attitude alteration control unit, the attitude of the distal end member and the attitude of the tool held by the distal end member can be properly maintained not only at the time of the initial attitude, but also at the time of alteration of the attitude.

The attitude control drive source is provided within the drive unit housing on the base end side of the spindle guide section and alteration of the attitude of the distal end member is carried out by remote control. Since the attitude altering member is inserted in the guide hole, it can properly act on the distal end member at all times with no displacement in position occurring in a direction transverse to the lengthwise direction of the attitude altering member and, therefore, the attitude altering operation of the distal end member is performed accurately.

In the present invention, the attitude of the distal end member can be determined in dependence on an amount of reciprocal movement of the attitude altering member relative to a reference position, which is defined as a position of the attitude altering member assumed when the distal end member is in the initial attitude. In such case, the remote controlled actuator of the present invention may be provided with an attitude setting device for setting a target attitude of the distal end member, in which the attitude alteration control unit is operable to convert the target attitude of the distal end member, preset by the attitude setting device, into an amount of advance or retraction of the attitude altering member, which corresponds thereto, and to change an amount of actuation of the attitude control drive source in dependence on the amount of advance or retraction so converted.

As described above, if the amount of actuation of the attitude control drive source is changed in accordance with the amount of advance or retraction of the attitude altering member, the control to alter the attitude of the distal end member can be simplified and is therefore facilitated.

Where as hereinabove described the attitude alteration control unit controls the attitude control drive source, it is recommended to use an actuation amount detector for detecting the amount of actuation of the attitude control drive source and feeding an output thereof back to the attitude alteration control unit.

The use of the actuation amount detector makes it possible to accurately detect the amount of actuation of the attitude control drive source and when the output thereof is fed back to the attitude alteration control unit, the control to alter the attitude can be performed accurately.

In the present invention, the remote controlled actuator may be further provided with a reverse input preventing mechanism for preventing the attitude control drive source from actuating by the effect of a force from the distal end member and, in such case, such reverse input preventing mechanism may be provided in the attitude control drive source or between the attitude control drive source and the distal end member. The reverse input preventing mechanism means an actuation transmitting mechanism, which transmits an input from an input end, but is unable to transmit an input from an output end. Blocking of transmission of a reverse input is accomplished by, for example, producing a difference in frictional resistance, which is brought about by the difference in direction of transmission of a force.

If the remote controlled actuator of the present invention is provided with the reverse input preventing mechanism, although during the supply of the electric power to the electrically driven actuator the attitude altering member advances or retracts, the attitude altering member will not advance or retract in a reverse direction even when the supply of the electric power is interrupted, and, hence, the thrust force obtained during the supply of the electric power can be maintained. In other words, at the time of advance or retraction, the electrically driven actuator has to be driven instantaneously with a high output. In contrast thereto, if no reverse input preventing mechanism is employed, a continuous output of the electrically driven actuator is required. For this reason, the use of the reverse input preventing mechanism makes it possible to use a compact motor for the electrically driven actuator. Also, not only can heat emission of the electrically driven actuator be suppressed, but also the heat radiating area of the electrically driven actuator can be minimized.

Where the reverse input preventing mechanism is employed in the remote controlled actuator of the present invention, the wording "initial attitude holding force necessary to enable the attitude of the distal end member to be held in an arbitrarily preset initial attitude" referred to above is to be understood as meaning a force transmitted to the attitude control drive source through the reverse input preventing mechanism. Also, the wording "force larger than the initial attitude holding force" referred to above is to be understood as meaning a force capable of altering the attitude of the distal end member through the reverse input preventing mechanism.

In the present invention, the attitude control drive source may be an electrically driven actuator and may be driven by an electric power of PWM wave.

If the electrically driven actuator is driven by the electric power of PWM (Pulse-Width Modulated) wave, the amount of the electric power supplied to the electrically driven actuator can be controlled easily and as a result, the drive of the electrically driven actuator can be controlled precisely.

In the present invention, the attitude control drive source can be a linear actuator. In such case, the remote controlled actuator may be provided with a force increasing and transmitting mechanism for increasing a thrust force of the linear actuator and then transmitting it to the attitude altering member, the force increasing and transmitting mechanism being comprised of a lever mechanism.

The use of the force increasing and transmitting mechanism is effective to allow even the linear actuator, having a small thrust force, to apply the large force to the attitude altering member and, therefore, the linear actuator can be reduced in weight.

Where the force increasing and transmitting mechanism in the form of the lever mechanism is employed, a strain sensor may be provided for detecting a strain occurring in the lever of the force increasing and transmitting mechanism and an external force estimating section for estimating an external force, acting on the distal end member, in reference to an output of the strain sensor.

The use of the strain sensor and the external force estimating section makes it possible to estimate the external force acting on the distal end member, and a result of such estimation can be utilized in the control to alter the attitude of the distal end member and/or a safety control or the like of the remote controlled actuator.

In the present invention, the remote controlled actuator may be further provided with an attitude altering operation piece provided outside the drive source housing for altering the attitude of the distal end member by causing an actuation command signal to be generated to the attitude control drive source through the attitude alteration control unit by means of an input manipulation, in which case the attitude altering operation piece is capable of accomplishing the input manipulation by hands then holding the drive unit housing.

The remote controlled actuator of the construction described above is such that while the drive unit housing is manually held, cutting of a site to be processed such as, for example, a bone is carried out with the rotating tool held in contact with the site to be processed. During the cutting, the attitude of the distal end member is altered to follow the shape or the like of the site to be processed. Since this attitude altering operation is performed by the attitude altering operation piece which is manipulatable by hands then used to hold the drive unit housing, the operator can feel the actual alteration of the attitude of the distal end member through his or her hands touching the operating pieced, and therefore, alteration of the attitude can be accurately and quickly accomplished.

In the present invention, the distal end member coupling unit supports the distal end member for tilting motion in arbitrary direction, in which case the guide hole and the attitude altering member inserted within the guide hole may be provided at three or more locations about a center of tilt of the distal end member and the attitude control drive source is provided for each of the attitude altering members and the attitude of the distal end member may be altered or maintained by an effect of balance of working forces applied from the attitude altering members at those three or more locations to the distal end member.

According to the above described construction, the attitude of the distal end member can be altered in two-axis directions.

Also, in the present invention, the distal end member coupling unit supports the distal end member for tilting motion in arbitrary directions, in which case the guide hole and the attitude altering member inserted within the guide hole may be provided at a plurality of locations about a center of tilt of the distal end member and the attitude control drive source is provided for each of the attitude altering members, a restoring elastic member for biasing the distal end member to hold a predetermined attitude is provided, and the plural attitude altering members may cooperate with each other to alter the attitude of the distal end member against a biasing force exerted by the restoring elastic member.

Even in this case, the attitude of the distal end member can be altered in two-axis directions.

Where as hereinabove described, the attitude of the distal end member can be altered about the two attitude altering axes, the attitude altering operation piece may be operable to alter the attitude of the distal end member in two directions when an actuation command signal is issued to each of the attitude control drive sources and may be manipulatable in two directions corresponding to directions in which the attitude of the distal end member is altered.

If the attitude altering operation piece is manipulatable in two directions corresponding to the directions in which the distal end member can be altered in attitude, the distal end member can be manipulated through the attitude altering operation piece so as to assume any arbitrary attitude.

In the present invention, a lock operating piece may be provided for disabling an input manipulation of the attitude altering operation piece.

The use of the lock operating piece makes it possible to avoid an accidental alteration of the attitude of the distal end member, which would otherwise result from an erroneous operation of the attitude altering operation piece.

In the present invention, an attitude detector may be provided for detecting the attitude of the distal end member and an attitude display section for displaying the attitude of the distal end member detected by the attitude detector.

The use of the attitude display section makes it possible to accurately grasp the attitude of the distal end member.

The attitude detector referred to above may be an encoder for detecting an actuation position of the attitude control drive source.

If the actuation position of the attitude control drive source is detected by the encoder, the attitude of the distal end member can be accurately detected.

In the present invention, the remote controlled actuator may be further provided with an attitude control section for controlling the attitude control drive source in dependence on an actuation command signal generated from the attitude altering operation piece.

The provision of the attitude control section makes it possible to change the relation between the actuation command signal, issued from the attitude altering operation piece, and the actuation of the attitude control drive source to suit to various conditions.

here may be provided an initial attitude operating piece for issuing an actuation command signal, necessary to cause the distal end member to assume the initial attitude, through the initial attitude hold control unit.

If the initial attitude operating piece is employed and the attitude control section includes the initial attitude hold control unit, the initial attitude of the distal end member can be set arbitrarily as desired, and also, the distal end member can be manually forcibly returned to the initial attitude. As a result, the initial attitude can be accurately resumed.

Also, a storage section may be provided for storing an actuation position of the attitude control drive source when the distal end member is in the initial attitude, in which case the initial attitude hold control unit of the attitude control section is operable to control the attitude control drive source so as to assume the actuation position, stored in the storage section, that when the initial attitude operating piece is operated.

The use of the storage section makes it possible to facilitate the control to reset the distal end member to the initial attitude, which is performed by the initial attitude hold control unit of the attitude control section.

In the present invention, the remote controlled actuator may be further provided with a rotation operating section for operating the rotation of the spindle, the rotation operating section being capable of being operated by hands then holding the drive unit housing.

If the rotation operating section is manually manipulatable by hands then holding the drive unit housing, rotation of the spindle and halt of the spindle then rotating can be performed readily at hand and as a result, the cutting process can readily be accomplished.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 2A is a sectional view showing a distal end member and a spindle guide section, both forming respective parts of the remote controlled actuator;

FIG. 2B is a cross sectional view taken along the line II-II in FIG. 2A;

FIG. 2C is a diagram showing a coupling structure with which the distal end member and a rotary shaft is coupled together;

FIG. 2D is a diagram showing a housing for the distal end member as viewed from a base end side thereof;

FIG. 7A is a sectional view showing the distal end member and the spindle guide section, both used in the remote controlled actuator according to a second preferred embodiment of the present invention;

FIG. 7B is a cross sectional view taken along the line VII-VII in FIG. 7A;

FIG. 13 is a block diagram showing a control system for the remote controlled actuator;

DESCRIPTION OF THE PREFERRED EMBODIMENTS

A first preferred embodiment of the present invention will now be described with particular reference to FIGS. 1 to 4.

Figure 1:
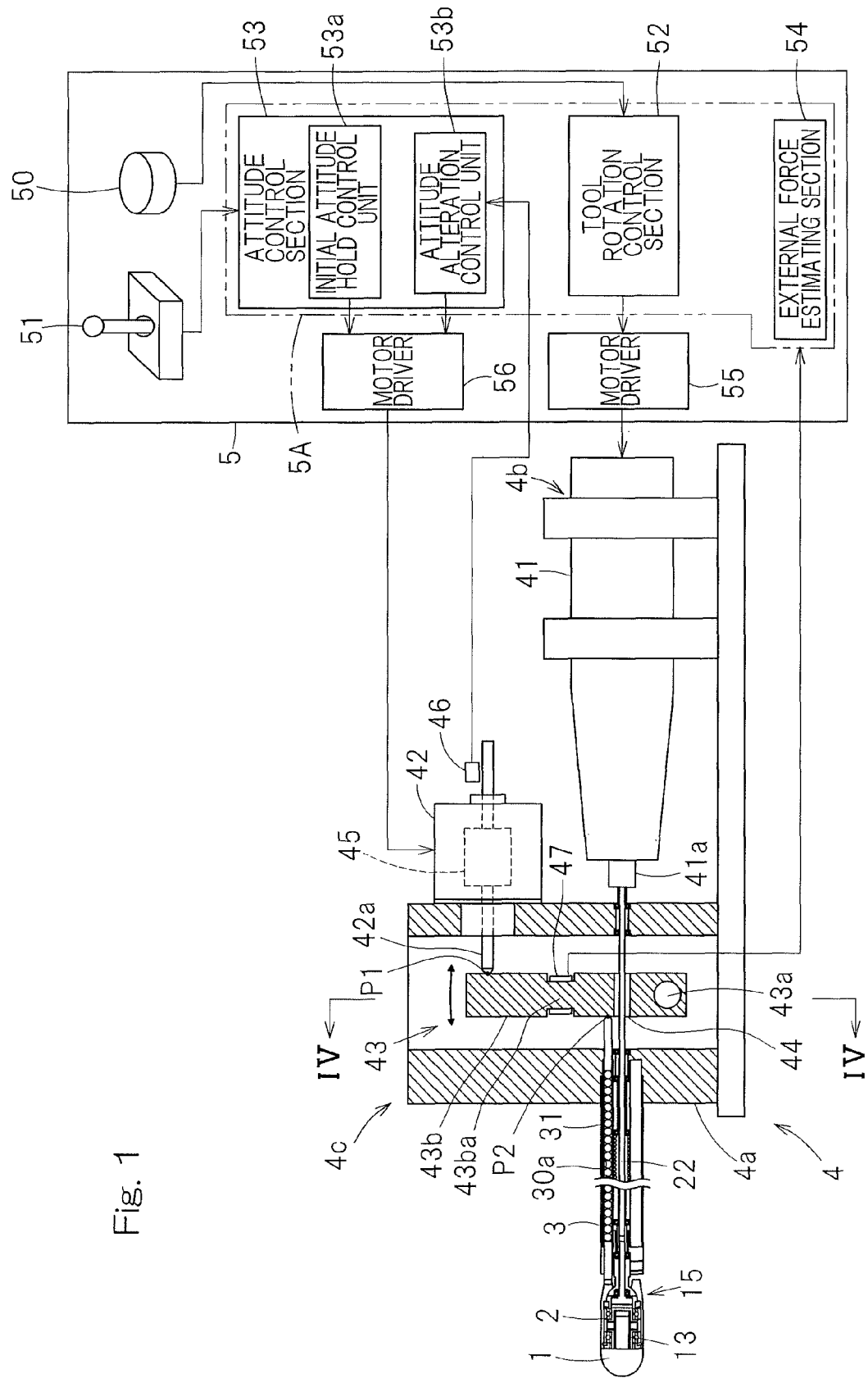
FIG. 1 is a diagram showing a remote controlled actuator in its entirety according to a first preferred embodiment of the present invention.

Referring to FIG. 1, a remote controlled actuator according to the first embodiment of the present invention includes a distal end member 2 for holding a rotary tool 1, an elongated spindle guide section 3 having a distal end to which the distal end member 2 is coupled for displacement in attitude, a drive unit housing 4a to which a proximal end of the spindle guide section 3 is coupled, and a controller 5 for controlling a tool rotating drive mechanism 4b and an attitude controlling drive mechanism 4c, both accommodated within the drive unit housing 4a. The drive unit housing 4a cooperates with the built-in tool rotating drive mechanism 4b and attitude altering drive mechanism 4c to form a drive unit 4.

Figure 3:
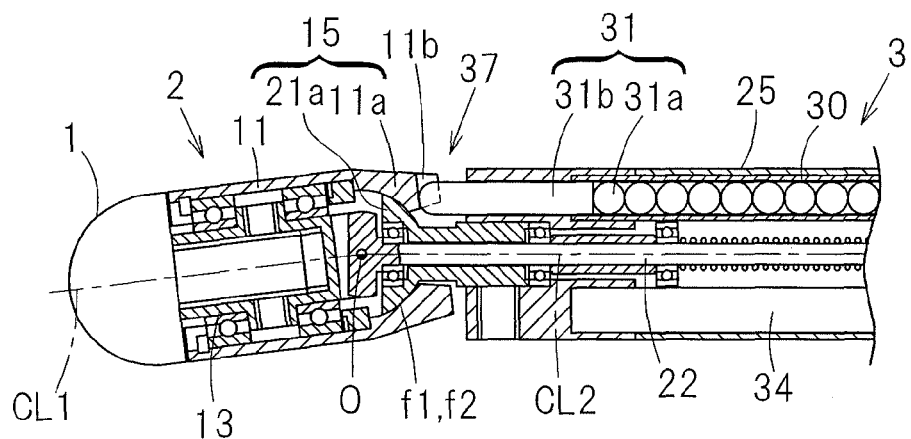
FIG. 3 is a sectional view showing the distal end member and the spindle guide section held in a condition different from that shown in FIG. 2A.

As best shown in FIGS. 2A to 2D and 3, the distal end member 2 includes a generally or substantially cylindrical housing 11 and a spindle 13 rotatably accommodated within such cylindrical housing 11 through a pair of bearings 12. The spindle 13 is of a tubular shape having a distal side opening and a shank portion 1a of the tool 1 is engaged with a splined portion 13a in an inner diameter of the spindle 13 with the shank portion 1a held non-detachably by means of a detent pin 14. The distal end member 2 is coupled with a distal end of the spindle guide section 3 through a distal end member coupling unit 15. The distal end member coupling unit 15 supports the distal end member 2 for displacement in attitude and is comprised of a spherical bearing. More specifically, the distal end member coupling unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces f1 and f2 that are held in sliding contact with each other, and those guide faces f1 and f2 have respective centers of curvature lying at a point O on the center line or longitudinal axis CL1 of the spindle 13 of the distal end member 2, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. FIGS. 2A to 2D illustrate the condition, in which the center line CL1 of the distal end member 2 and the center line CL2 of the spindle guide section 3 are concentric with each other and are therefore represented by the same line. FIG. 3 illustrates the condition in which those two center lines CL1 and CL2 are held at an angle relative to each other.

The spindle guide section 3 includes therein a rotary shaft 22 for transmitting a rotational force, exerted by a tool rotating drive source 41 (FIG. 1) accommodated within the drive unit housing 4a, to the spindle 13. In the illustrated example, the rotary shaft 22 is employed in the form of a wire and is capable of undergoing elastic deformation to a certain extent. Material for the wire includes, for example, metal, resin or glass fiber. The wire may be either a single wire or a twisted wire. As best shown in FIG. 2C, the spindle 13 and the rotary shaft 22 are connected together by means of a joint 23 such as, for example, an universal joint for transmitting rotation from the rotary shaft 22 to the spindle 13. The joint 23 includes a groove 13b, defined in a closed base end of the spindle 13, and a projection 22a defined in a distal end of the rotary shaft 22 and engageable in the groove 13b. The center of joint between the groove 13b and the projection 22a is located at the same position as the centers of curvature O of the guide faces f1 and f2. It is, however, to be noted that the rotary shaft 22 and the projection 22a may be formed of members separate from each other.

The spindle guide section 3 includes an outer shell pipe 25 forming an outer shell of the spindle guide section 3 and the rotary shaft 22 referred to above is positioned at the center of this outer shell pipe 25. The rotary shaft 22 so positioned is rotatably supported by a plurality of rolling bearings 26 positioned spaced a distant apart from each other in a direction axially of the spindle guide section 3. Spring elements 27A and 27B for generating preloads on the corresponding rolling bearings 26 are disposed between the neighboring rolling bearings 26. Each of those spring elements 27A and 27B is employed in the form of, for example, a compression spring. There are the spring element 27A for inner ring for generating the preload on the inner ring of the rolling bearing 26 and the spring element 27B for outer ring for generating the preload on the outer ring of the rolling bearing 26, and the both 27A and 27B are arranged alternately relative to each other. The constraint member 21 referred to previously is fixed to a pipe end portion 25a of the outer shell pipe 25 by means of a fixing pin 28 and has its distal end inner peripheral portion supporting the distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

As best shown in FIG. 2B, three guide pipes 30 are interposed between an inner diametric surface of the outer shell pipe 25 and the rotary shaft 22 so as to extend between the both ends and are positioned at respective circumferential position spaced 120° in phase from each other within the outer shell pipe 25. Also, attitude altering or operating members 31 (31U, 31L and 31R), each made up of a plurality of balls 31a and pillar shaped pins 31b at opposite ends, both of which form a force transmitting member, are axially movably inserted within respective guide holes 30a of guide pipes 30, which guide holes 30a are represented by respective inner diametric holes of those guide pipes 30. The balls 31a and the pillar shaped pins 31b are arranged in a row in line with each other in a direction lengthwise of the guide hole 30a with no gap formed between those elements. One of the pillar shaped pins 31b, which is on the side of the distal end member 2, has its tip representing a spherical shape and held in contact with a bottom surface of a groove 11b formed in a base end face of the housing 11. The groove 11b and the pillar shaped pin 31b altogether form a rotation preventing mechanism 37, which serves to prevent the distal end member 2 from rotating about the center line CL1 of the distal end member 2 relative to the spindle guide section 3 when a tip end portion of the pillar shaped pin 31b engaged in the groove 11b is brought into engagement with a side face of the groove 11b. The pillar shaped pin 31b on the drive unit housing 4a also has its tip representing a spherical shape and engaged with a side face of a lever 43b as will be described in detail later.

Also, between the inner diametric surface of the outer shell pipe 25 and the rotary shaft 2, a plurality of reinforcement shafts 34 are arranged separate from the guide pipes 30 and on the pitch circle C of the same diameter as the guide pipes 30. Those reinforcement shafts 34 are used to secure the rigidity of the spindle guide section 3. The guide pipes 30 and the reinforcement shafts 34 are arranged equidistantly relative to each other around the rotary shaft 22. The guide pipes 30 and the reinforcement shafts 34 are held in contact with the inner diametric surface of the outer shell pipe 25 and respective outer peripheral surfaces of the rolling bearings 26. In this manner, the outer diametric surfaces of those rolling bearings 26 are supported.

Figure 4:
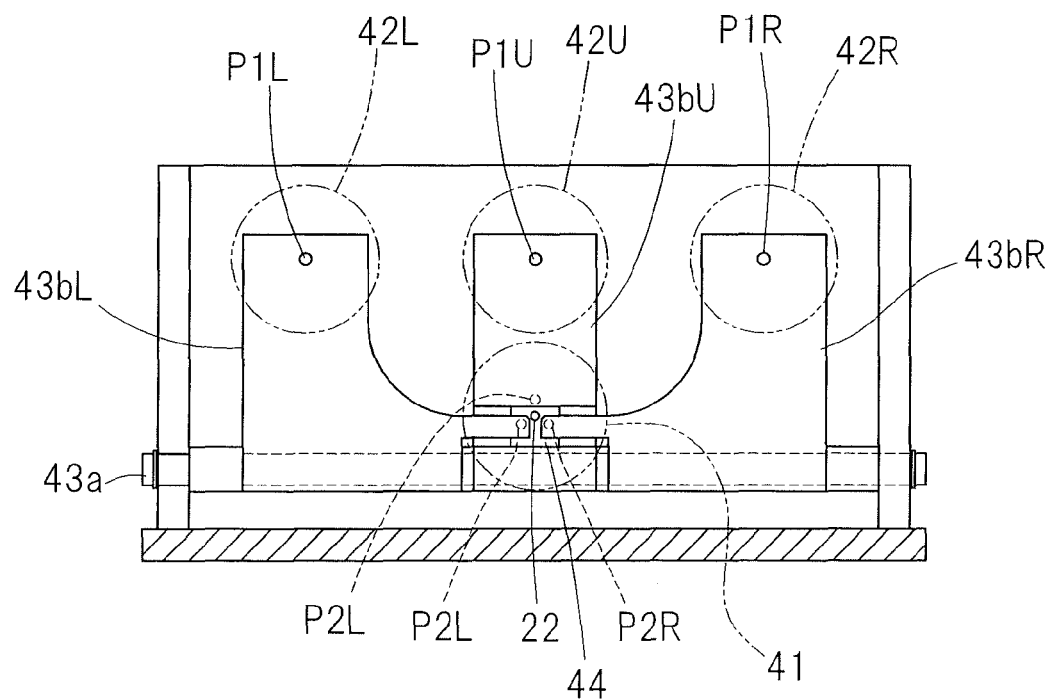
FIG. 4 is a cross sectional view taken along the line IV-IV in FIG. 1.

As best shown in FIGS. 1 and 4, the tool rotating drive mechanism 4b includes a tool rotating drive source 41. This tool rotating drive source 41 is in the form of, for example, an electric motor, having its output shaft 41a coupled with a base end or proximal end of the rotary shaft 22. The attitude control drive mechanism 4c includes three attitude control drive sources 42 (42U, 42L and 42R) cooperable respectively with attitude altering members 31 (31U, 31L and 31R). The attitude control drive sources 42 are in the form of electrically driven linear actuators driven by an electric power of PWM (Pulse-Width Modulated) waves and the rotary motion of a rotary motor (not shown) built therein is transmitted to an output rod 42a after having been converted into a linear motion by means of a rotary-linear motion translating mechanism, which concurrently serves as a reverse input preventing mechanism 45. The output rod 42a is movable in a direction leftward and rightward as viewed in FIG. 1 and the amount of movement of the output rod 42a, that is, the amount of actuation of the attitude control drive source 42 is detected by an actuation amount detector 46, which is in the form of an encoder.

For the rotary-linear motion translating mechanism, a feed screw mechanism of a sliding screw type such as, for example, a triangular screw or a trapezoidal screw can be employed. Because of the use of the feed screw mechanism of such a sliding screw type, the attitude control drive source 42 has a reverse input preventing function to avoid a possible operation caused by a force from the attitude altering member 31. For the rotary-linear motion translating mechanism, a ball screw or a rack and pinion mechanism may be employed other than the sliding screw type. In such case, the reverse preventing mechanism 45 has to be employed separately. For the reverse input preventing mechanism 45 employed in such case, a worm gear or the like can be employed. Other than those, a speed reducer having a large gear ratio can also be employed.

It is to be noted that the reverse input preventing mechanism 45 may not necessarily be provided in the attitude control drive source 42, but may be provided somewhere in the attitude control drive mechanism 4c, that is, between the attitude control drive source 42 and the attitude altering member 31.

The linear movement of the output rod 42a is transmitted to the attitude altering member 31 through a force increasing and transmitting mechanism 43. The force increasing and transmitting mechanism 43 includes a pivot lever 43b pivotable about a support pin 43a and is so designed and so configured as to allow a force of the output rod 42a to work on a working point P1 of the lever 43b, which is spaced a long distance from the support pin 43a, and as to apply a force to the attitude altering member 31 at a force point P2, which is spaced a short distance from the support pin 43a, wherefore an output of the attitude altering drive source 42 can be increased and then transmitted to the attitude altering member 31. A strain inducing portion 43ba having a small wall thickness is provided at an intermediate portion of the lever 43b and a strain sensor 47 for detecting the strain generated in the strain inducing portion 43ba is fitted to each of the opposite sides of the strain inducing portion 43ba. The rotary shaft 22 is passed through an opening 44 defined in the lever 43b.

The controller 5 includes a computer 5A, a manually operable rotational speed setting device 50 for manually providing an input to the computer 5A and an attitude setting device 51. The rotational speed setting device 50 is used to set a rotational speed of the spindle 13. The attitude setting device 51 is used to set an target attitude that is to be assumed by the distal end member 2 relative to the spindle guide section 3. The computer 5A of the controller 5 in turn includes a tool rotation control section 52 for controlling the tool rotating drive source 41, an attitude control section 53 for controlling each of the attitude control drive sources 42 and an external force estimating section 54 for estimating an external force acting on the distal end member 2.

The tool rotation control section 52 is operable to provide a motor driver 55 with an output signal in correspondence with an input signal from the rotational speed setting device 50 to thereby drive the tool rotating drive source 41.

The attitude control section 53 includes an initial attitude hold control unit 53a and an attitude alteration control unit 53b. The initial attitude hold control unit 53a and the attitude alteration control unit 53b are operable to supply respective output signals to a motor driver 56 in correspondence with an input signal or the like from the attitude setting device 51 to thereby drive the attitude control drive sources 42.

The initial attitude hold control unit 53a is operable to control each of the attitude control drive sources 42 so that an initial attitude holding force F0 (FIG. 5) for enabling the distal end member 2 to hold an arbitrarily preset initial attitude can be applied to the attitude altering member 31. The attitude of the distal end member 2 is determined by the balance between the external force, acting on the distal end member 2, and a thrust force of each of the attitude control drive sources 42. In view of this, when the attitude control drive sources 42 are so controlled as to apply the initial attitude holding force F0 to the attitude altering member 31, the distal end member 2 can be held in the initial attitude. Holding of the attitude of the distal end member 2, that is, securement of the rigidity of the distal end member 2 is accomplished by the thrust force of the attitude control drive sources 42. Thus, where no force necessary to alter the attitude is applied, the rigidity is applied by the initial attitude hold control unit 53a so that the distal end member can 2 resume and maintain the arbitrarily preset initial attitude.

Figure 5:
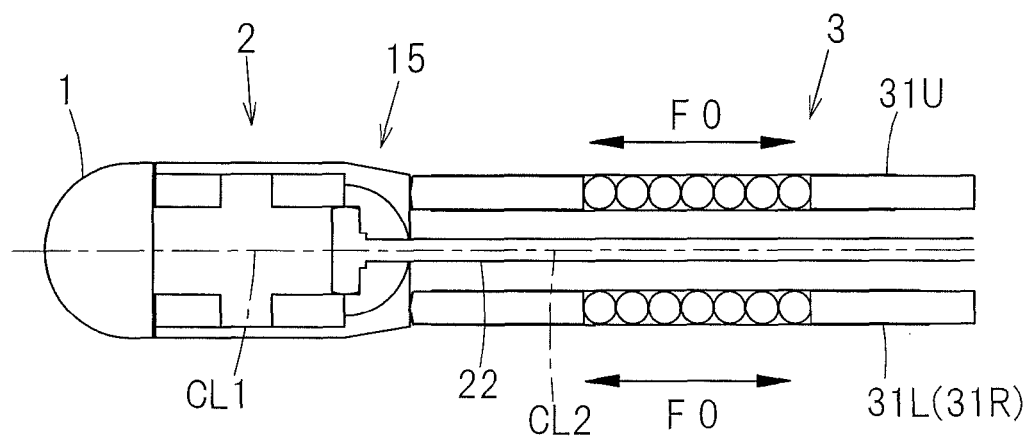
FIG. 5 is an explanatory diagram showing a force acting on an attitude altering member and a distal end member coupling unit when the distal end member of the remote controlled actuator is in the initial attitude setting.
Figure 6:
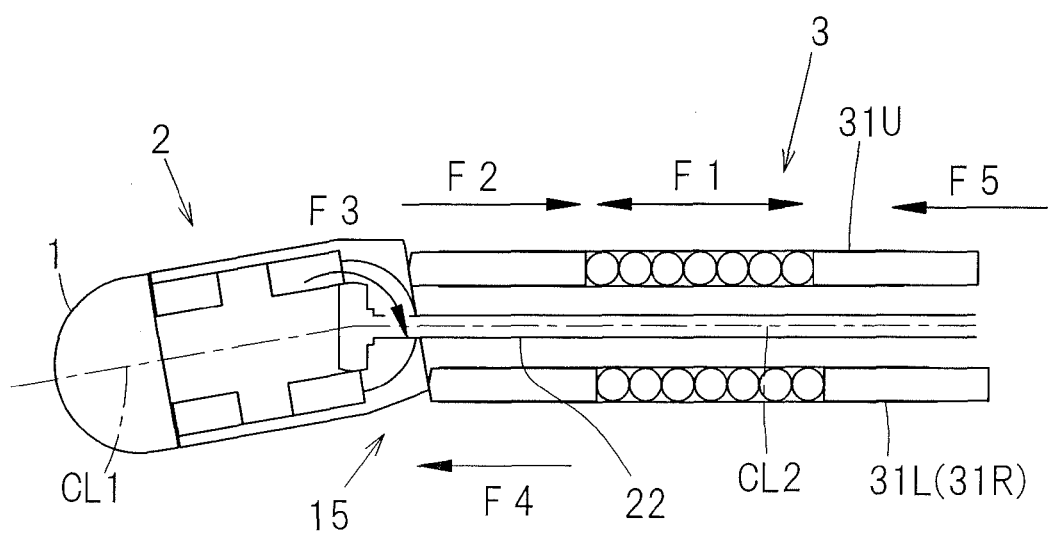
FIG. 6 is an explanatory diagram showing the force acting on the attitude altering member and the distal end member coupling unit when the distal end member of the remote controlled actuator is to be changed in attitude.

The arbitrarily preset initial attitude referred to above may be either an attitude, in which the center line CL1 of the distal end member 2 and the center line CL2 of the spindle guide section 3 are concentrically aligned with each other as shown in FIG. 5, or an attitude in which the center line CL1 of the distal end member 2 and the center line CL2 of the spindle guide section 3 are at an angle relative to each other and are therefore bent relative to each other as shown in FIG. 6.

The attitude alteration control unit 53b referred to above is operable to control each of the attitude control drive sources 42 so that a force F5 larger than the initial attitude holding force F0 referred to previously can be applied to the attitude altering member 31 to selectively advance or retract the attitude altering member 31 to thereby change the attitude of the distal end member 2. When the attitude of the distal end member 2 is to be altered, a force larger than that during sustainment of the initial attitude, that is, during the standstill acts on the distal end member 2 as will be described in detail later. Accordingly, when the attitude of the distal end member 2 is to be altered, the attitude control drive source 42 is so controlled as to enable the force F5, larger than the previously described initial attitude holding force F0 necessary to maintain the attitude of the distal end member 2, to be applied to the attitude altering member 31. The attitude of the distal end member 2 is determined by the amount of advance or retraction of the attitude altering member 31 relative to a reference position, which is the position of the attitude altering member 31 assumed when the distal end member 2 is in the initial attitude.

More specifically, the attitude alteration control unit 53b is operable to convert the target attitude of the distal end member 2 relative to the previously described initial attitude preset by the attitude setting device 51, into the amount of advance or retraction of the attitude altering member 31, which corresponds to the target attitude, and then to change the amount of actuation of the attitude control drive source 42 in dependence on the converted amount of advance or retraction. Since the amount of actuation of the attitude control drive source 42 is changed in dependence on the amount of advance or retraction of the attitude altering member 31, the attitude altering control of the distal end member 2 can be simplified and facilitated.

Also, when the above described control takes place, control is effected by feeding the amount of actuation of the attitude control drive source 42, then detected by the actuation amount detector 46, back to the attitude alteration control unit 53b. The provision of the actuation amount detector 46 is effective to enable the amount of actuation of the attitude control drive source 42 to be detected accurately and, when an output therefrom is fed back to the attitude alteration control unit 53b, the attitude altering control can be accomplished accurately.

The external force estimating section 54 referred to previously includes a relation setting module (not shown), in which a relation between the external force acting on the distal end member 2 and the respective output signals of the strain sensors 47 are set in terms of an arithmetic expression and/or a table or the like, and utilizes the relation setting module to estimate the external force, then acting on the distal end member 2, from respective signals inputted from the strain sensors 47.

The operation of the remote controlled actuator of the structure hereinabove described will now be described.

When the tool rotation drive source 41 is driven, a rotational force thereof is transmitted to the spindle 13 through the rotary shaft 22, accompanied by rotation of both of the spindle 13 and the tool 1. By the tool 1 so rotated, cutting of the bone takes place.

When the distal end member 2 is in the initial attitude, each of the attitude control drive sources 42 is controlled by means of the initial attitude hold control unit 53a so as to maintain the distal end member 2 in the initial attitude. At this time, the predetermined initial attitude holding force F0, composed of the thrust force of the attitude control drive source 42, and a reactive force thereto act on each of the attitude altering members 31 as shown in FIG. 5. FIG. 5 is a diagram corresponding to a simplified form of the cross section taken along the line V-CL2-V in FIG. 2B, and only the upper and left attitude altering members 31U and 31L are shown. As a matter of course, the initial attitude holding force F0 referred to above equally acts on the right attitude altering member 31R which is not shown in FIG. 5. Thus, when the initial attitude holding force F0 is applied to each of the attitude altering members 31, the balance of the forces acting on the distal end member 2 can be preserved and the attitude of the distal end member 2 can therefore be maintained.

During the use, each of those attitude control drive sources 42 is driven and the attitude of the distal end member 2 is altered by remote control. By way of example, when one of the attitude altering members 31, i.e., the attitude altering member 31U, which is positioned in an upper area in FIGS. 2A to 2D, is advanced towards a tip end side while the remaining two attitude altering members 31L and 31R are retracted, the housing 11 of the distal end member 2 is pressed by the upper attitude altering member 31U with the attitude of the distal end member 2 being consequently altered along the guide faces f1 and f2. Thus, the tip end side can be oriented downwards as shown in FIG. 2A, thereby assuming the condition as shown in FIG. 3. It is to be noted that the attitude altering members 31L and 31R are, when the attitude control drive sources 42L and 42R are driven in respective directions reverse to the direction in which the attitude control drive source 42U is driven, retracted by the housing 11 of the distal end member 2 then pressing such attitude altering members 31L and 31R.

Also, when, while the upper attitude altering member 31U is held standstill, the left attitude altering member 31L is advanced towards the tip end side and, on the other hand, the right attitude altering member 31R is retracted, the housing 11 of the distal end member 2 is pressed by the left attitude altering member 31L with the distal end member 2 consequently oriented rightwards, that is, towards a side reverse to the plane of the sheet of FIG. 2A along the guide faces f1 and f2, thus changing the attitude.

Because of the provision of the attitude altering members 31 at three locations in the circumferential direction, the distal end member 2 can be altered in attitude in two-axis directions (X-axis and Y-axis direction) i.e., upwards or downwards and leftwards or rightwards.

The pressures from the three attitude altering members 31 and the reactive force from the constraint member 21 act on the distal end member coupling unit 15, and depending on the balance of those working forces, the attitude of the distal end member 2 is determined. Since the housing 11 of the distal end member 2 is pressed by those three attitude altering members 31, the attitude stability of the distal end member 2 is high.

Taking the attitude alteration of the distal end member 2 around the X-axis for instance, the thrust force of the attitude control drive source 42U that is required for the attitude alteration will now be discussed in detail. FIG. 6 illustrates forces F1 to F5 which act on each of the attitude altering members 31 and the distal end member coupling unit 15 at the time of alteration of the attitude of the distal end member 2. F1 represents an attitude holding force and a reactive force thereof, which act on the upper attitude altering member 31U at the time of alteration of the attitude. The attitude holding force referred to above is comprised of a thrust force of the attitude control drive source 42. F2 represents a frictional force generated when the upper attitude altering member 31U is advanced towards the tip end side. F3 represents a frictional force generated between the guide faces f1 and f2 of the distal end member coupling unit 15. F4 represents a frictional force generated when the left and right attitude altering members 31L and 31R are retracted. More specifically, respective frictional forces are generated in the left and right attitude altering members 31L and 31R and the sum of those frictional forces in the attitude altering members 31L and 31R is represented by the force F4. F5 represents the thrust force of the attitude control drive source 42U required to advance the upper attitude altering member 31U towards the tip end side. The following relations establish among those forces F1 to F5:

$$F5 > F2 + F3 + F4 + F1 \quad (1)$$

Since F1≈F0 (initial attitude holding force), the equation (1) above can be rewritten as follows:

$$F5 > F2 + F3 + F4 + F0 \quad (2)$$

In other words, the thrust force F5 of the attitude control drive source 42U is greater than the initial attitude holding force F0 to which the various frictional forces F2, F3 and F4 are added. For example, the thrust force F5 is about twice the initial attitude holding force F0. As described above, when the attitude control drive source 42U is so controlled that the force F5, which is greater than the initial attitude holding force F0, can be applied to the attitude altering member 31U, the distal end member 2 can be altered in attitude.

As discussed above, when the attitude of the distal end member 2 during the standstill condition is controlled by the initial attitude hold control unit 53a and the attitude of the distal end member 2 during the alteration of the attitude is controlled by the attitude alteration control unit 53b, the attitude of the distal end member 2 and the attitude of the tool 1 held thereby can be properly maintained not only during the standstill but also during the attitude alteration.

As hereinabove described, the attitude control drive source 42 is driven by an electric power of the PWM wave and has a reverse input preventing function. Accordingly, the attitude altering member 31U operates in the following manner. In other words, while the attitude altering member 31U advances when the PWM wave is ON (active with an electric power supplied), due to the reverse input preventing function, the attitude altering member 31U does not retract even when the PWM wave is OFF (inactive with the supply of the electric power interrupted) and the advanced position is maintained when the PWM wave is ON. In other words, the attitude altering member 31U undergoes continuous repetition of minute advances. In contrast thereto, if there is no reverse input preventing function in the attitude control drive source 42, the attitude altering member 31U retracts when the PWM wave is OFF, and, therefore, the amount of actuation of the attitude altering member 31U represents an average between the amount of advance, effected when the PWM wave is ON, and the amount of retraction effected when the PWM wave is OFF. Accordingly, as compared with the case of the reverse input preventing function not provided in the attitude control drive source 42, the structure according to the foregoing embodiment of the present invention is effective to secure a large amount of actuation as a whole. For this reason, a compact motor can be advantageously employed in the attitude control drive source 42, which is an electrically driven actuator. Also, not only can the heat emission from the attitude control drive source 42 be suppressed, but also a heat dissipating unit of the attitude control drive source 42 can be fabricated in a compact size.

Yet, as best shown in FIG. 1, since the force increasing and transmitting mechanism 43 is provided, the large force can be applied to the attitude altering member 31 even with the attitude control drive source 42 capable of exerting a small thrust force. In view of this, the attitude control drive source 42 can be fabricated in a compact size.

When an external force acts on the distal end member 2 or the tool 1 during the cutting operation, a force thereof is transmitted to the lever 43b of the force increasing and transmitting mechanism 43 through the attitude altering member 31, resulting in strain in the strain inducing portion 43ba, which is a fragile portion. This strain is in turn detected by the strain sensor 47 and an output signal thereof is transmitted to the external force estimating section 54. The external force estimating section 54 estimates the external force, then acting on the distal end member 2, from the output signal of the strain sensor 47. When the amount of feed of the remote controlled actuator as a whole and the alteration of the attitude of the distal end member 2 are controlled in dependence on the magnitude of the external force estimated in the manner as hereinabove described, the bone can be cut securely and accurately while the external force acting on the distal end member 2 is properly maintained.

Also, the rotation preventing mechanism 37 prevents the distal end member 2 from rotating about the center line CL1 of the distal end member 2 relative to the spindle guide section 3. Accordingly, even when the distal end member 2 then holding the tool 1 becomes unable to be controlled by reason of a trouble occurring in the attitude control section 53 and/or the attitude operating drive mechanism 4c for controlling the selective advance and retraction of the attitude altering member 31, it is possible to avoid the possibility that the site to be processed may be impaired as a result of rotation of the distal end member 2 about the center line CL1 or the distal end member 2 itself may be broken.

Since the attitude altering member 31 is inserted through the guide hole 30a, the attitude altering member 31 can act properly on the distal end member 2 at all times without being accomplished by displacement in position in a direction perpendicular to the lengthwise direction thereof, and therefore, the attitude altering operation of the distal end member 2 can be performed accurately. Also, since the attitude altering member 31 includes the plurality of the balls 31a and the pillar shaped pins 31b and has a flexible property in its entirety, the attitude altering operation of the distal end member 2 is assuredly carried out even though the spindle guide section 3 is curved. In addition, since the center of the junction between the spindle 13 and the rotary shaft 22 lies at the same position as the respective center of curvature O of the guide faces f1 and f2, no force tending to press and pull will act on the rotary shaft 22 as a result of alteration of the attitude of the distal end member 2 and, therefore, the distal end member 2 can be altered in attitude smoothly.

The remote controlled actuator according to the embodiment is used in grinding the femoral marrow cavity during, for example, the artificial joint replacement surgery and during the surgery, it is used with the distal end member 2 in its entirety or a part thereof inserted into the body of a patient. For this reason, if the distal end member 2 can be altered in attitude by remote control, the bone can be processed in a condition with the tool 1 maintained in a proper attitude at all times and, therefore, the opening for insertion of the artificial joint can be finished precisely.

There is necessity that the rotary shaft 22 and the attitude altering member 31 are provided in a protected fashion. In this respect, the spindle guide section 3, which is elongated in shape, is provided with the rotary shaft 22 at the center of the outer shell pipe 25 and the guide pipes 30, accommodating therein the attitude altering member 31, and the reinforcement shafts 34, all of these are arranged in the circumferential direction and between the outer shell pipe 25 and the rotary shaft 22. Accordingly, the rotary shaft 22 and the attitude altering member 31 are protected and the interior can be made hollow to thereby reduce the weight without sacrificing the rigidity. Also, the arrangement balance as a whole is rendered good.

Since the outer diametric surfaces of the rolling bearings 26 supporting the rotary shaft 22 are supported by the guide pipes 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 in the form of a wire can be rotated at a high speed. For these reasons, since the processing can be accomplished with the spindle 13 rotated at a high speed, a good finish of the processing can also be obtained and further, the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

While the foregoing embodiment has been shown and described, in which each of the guide pipe 30 and the attitude altering member 31 is provided at three locations in the circumferential direction, the present invention is equally applicable to the arrangement, in which each of the guide pipe 30 and the attitude altering member 31 is arranged at two locations within the outer shell pipe 25 in a fashion spaced 180° in phase from each other in the circumferential direction as shown in FIGS. 7A and 7B showing a second preferred embodiment of the present invention. In such case, the distal end member 2 can be altered in attitude only about the X-axis.

A third preferred embodiment of the present invention will be hereinafter described in detail with particular reference to FIGS. 8 to 16. In the third embodiment shown in FIGS. 8 to 16, component parts similar to or identical with those shown and described in connection with the first embodiment of the present invention are designated by like reference numerals used therein and the details are not reiterated for the sake of brevity. The remote controlled actuator shown in FIG. 8 and pertaining to the third embodiment of the present invention is made up of an actuator body 6 and a control box 7 connected with the actuator body 6 through an electric cable 8.

The actuator body 6 is made up of a distal end member 2 for holding the rotary tool 1, which has been described in connection with the previously described first embodiment of the present invention, an elongated spindle guide section 3 having the distal end member 2 fitted to a distal end of thereof for alteration in attitude, and a drive unit housing 4a to which a base end of the spindle guide section 3 is coupled. The drive unit housing 4a cooperates with the built-in tool rotating drive mechanism 4b and an attitude altering drive mechanism 4c to define a drive unit 4.

The distal end member 2 and the spindle guide section 3, both employed in the remote controlled actuator according to the third embodiment of the present invention, are similar to those shown in and described with reference to FIGS. 2A to 2D in connection with the previously described first embodiment and the details thereof are not therefore reiterated for the sake of brevity.

Figure 9:
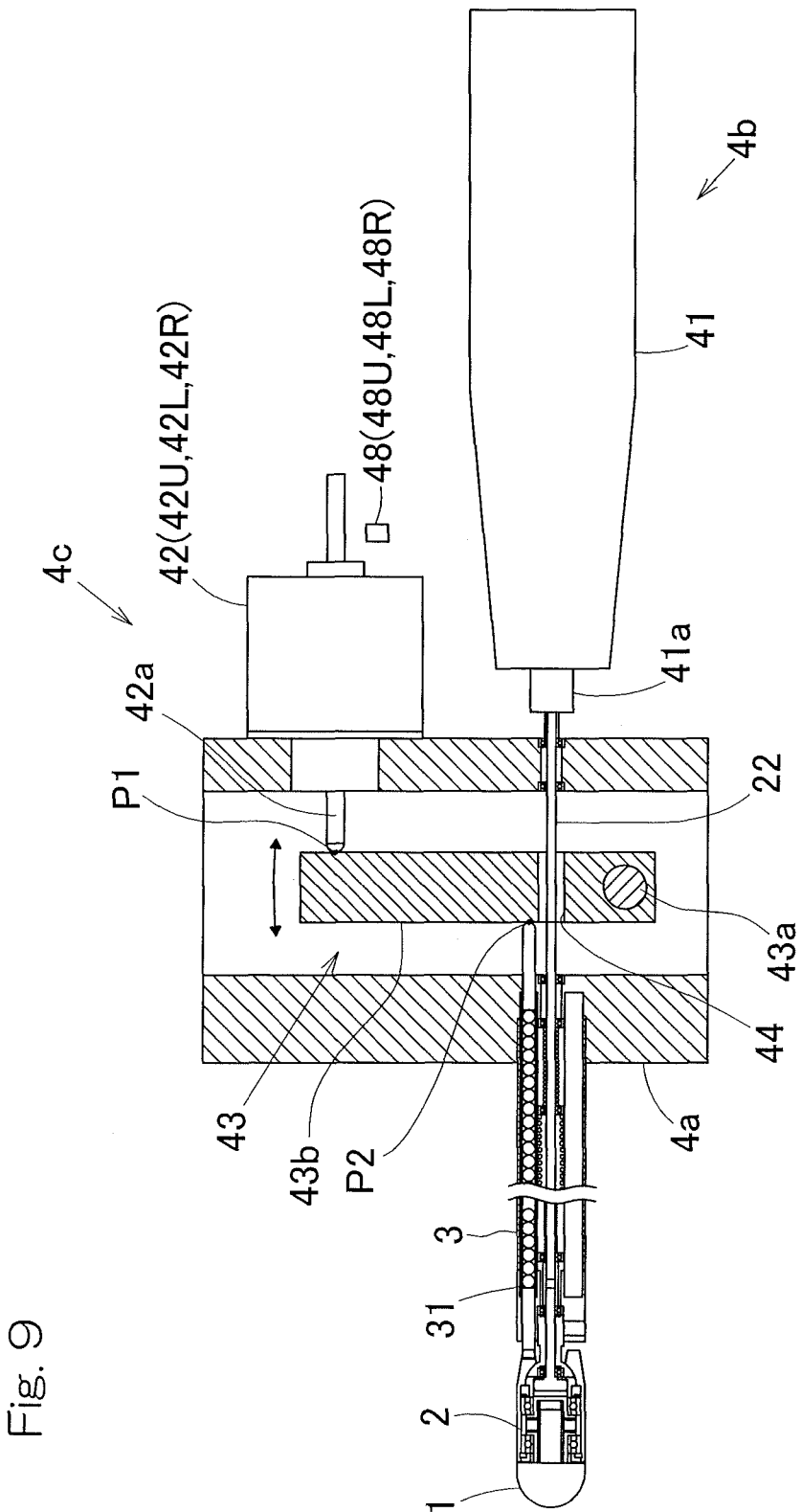
FIG. 9 is a sectional view showing the structure employed mainly within a drive unit housing of the remote controlled actuator.

The attitude altering drive mechanism 4c referred to above includes three attitude control drive sources 42 (42U, 42L and 42R) corresponding respectively to the attitude altering members 31 (31U, 31L and 31R) in a manner similar to those employed in the previously described first embodiment. The attitude control drive sources 42 are employed in the form of, for example, electrically driven linear actuators and movement of an output rod 42a thereof movable leftwards and rightwards as viewed in FIG. 9 is transmitted to the attitude altering member 31 through the force increasing and transmitting mechanism 43. The position of selective advance or retraction of the output rod 42a of each of the attitude altering members 31, that is, the position of activation of each of the attitude control drive sources 42, is detected respectively by an attitude detector 48 (48U, 48L and 48R) each in the form of an encoder. This attitude detector 48 is of a type capable of performing the same detecting operation as the activation amount detector 46 shown in FIG. 1.

Figure 8:
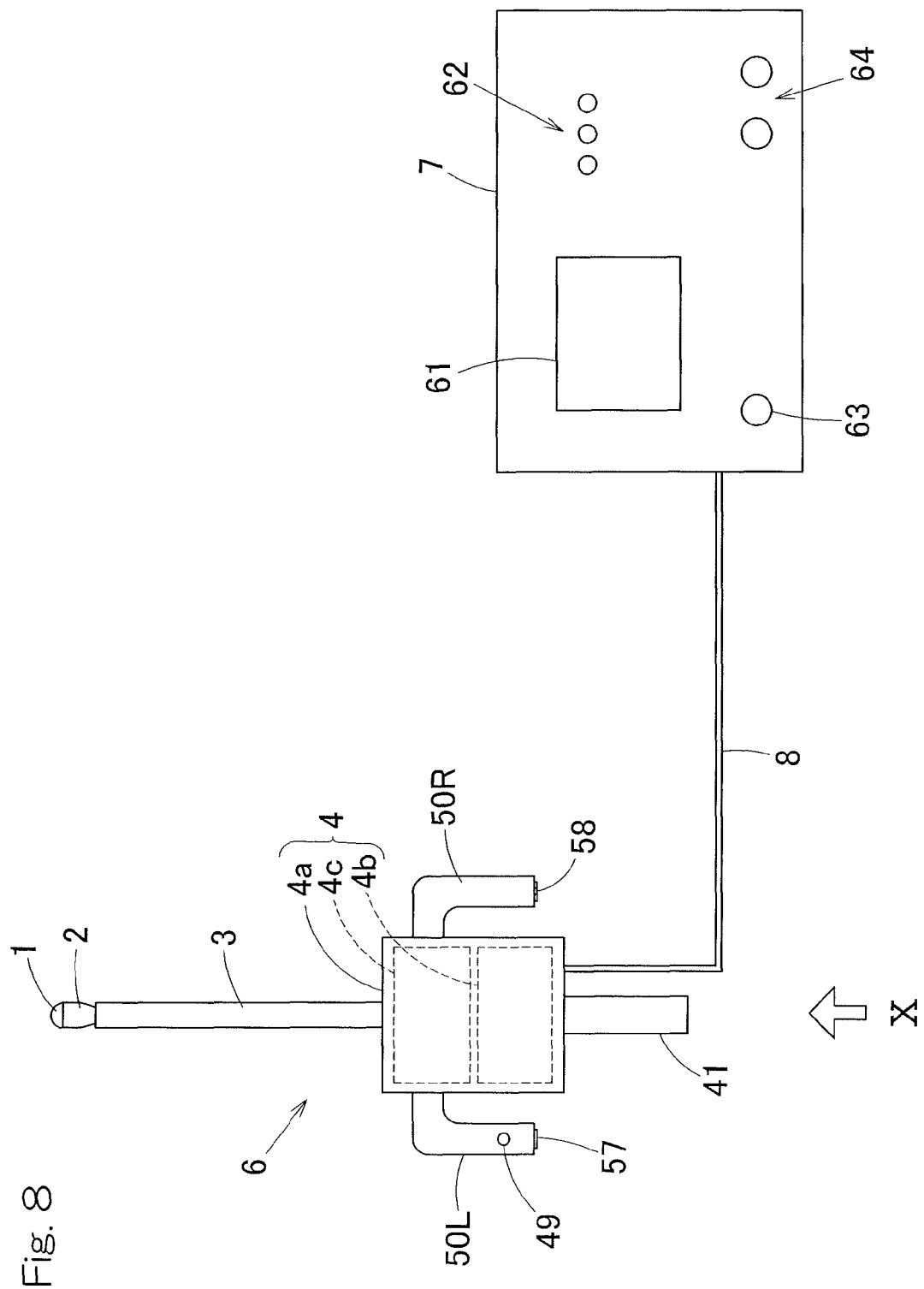
FIG. 8 is a diagram showing a schematic structure of the remote controlled actuator according to a third preferred embodiment of the present invention.
Figure 10:
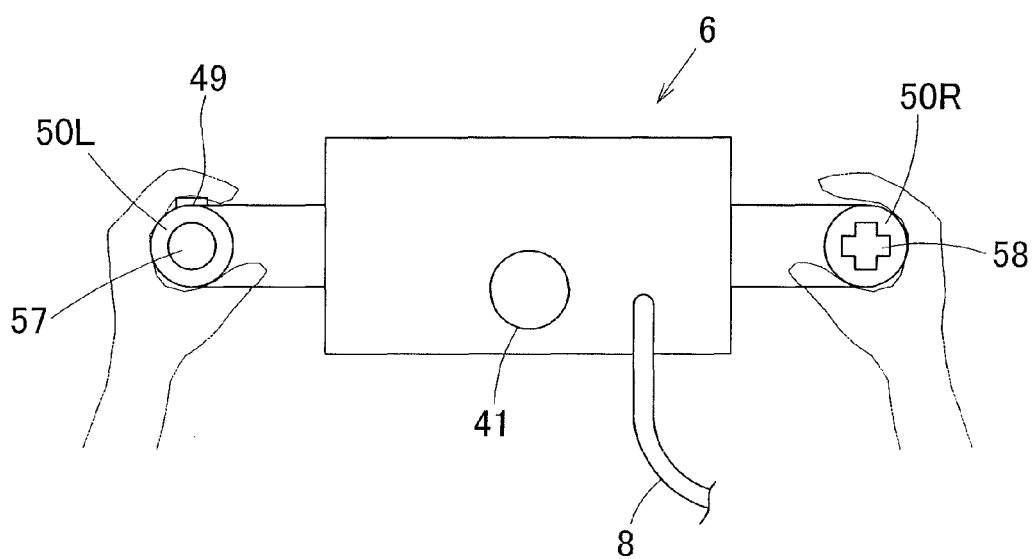
FIG. 10 is a view showing the remote controlled actuator as viewed in a direction shown by X in FIG. 8.

As shown in FIGS. 8 and 10, left and right side faces of the drive unit housing 4a is provided with a pair of left and right handles 50L and 50R. As shown by the double dotted chain line in FIG. 10, the actuator body 6 can be held with the handles 50L and 50R gripped by opposite hands.

The left handle 50L has a tip end provided with a rotation ON/Off operating piece 57, or a rotation operating section, for selectively rotating or halting the spindle 13. Also, the left handle 50L has an upper face provided with a lock operating piece 49 for halting the function of an attitude altering operation piece 58 as will be described in detail later. Each of the rotation ON/OFF operating piece 57 and the lock operating piece 49 is in the form of a push button switch and can be manipulated by a left hand then gripping the left handle 50L.

Figure 11:
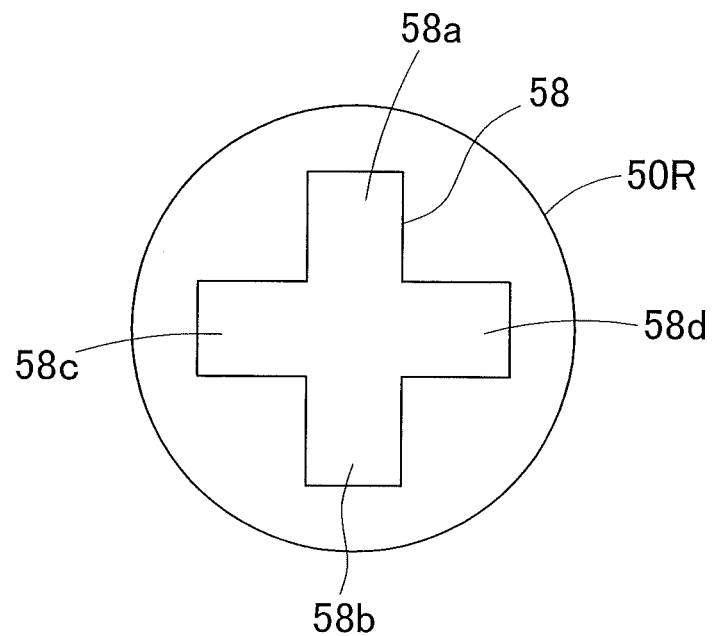
FIG. 11 is a fragmentary enlarged view a portion of FIG. 10, showing an attitude altering tool employed in the remote controlled actuator.

The right handle 50R has its tip end provided with the attitude altering operation piece 58 for altering the attitude of the distal end member 2. As shown in FIG. 11 on an enlarged scale, the attitude altering operation piece 58 is a crisscross switch having four operating pieces arranged in a cross form and those four operating pieces are represented respectively by an upper tilt operating piece 58a for tilting the distal end member 2 so as to be oriented upwardly, a lower tilt operating area 58b for tilting it so as to be oriented downwardly, a left tilt operating piece 58c for tilting it so as to be oriented leftwards, and a right tilt operating piece 58d for tilting it so as to be oriented rightwards. Those operating pieces 58a, 58b, 58c and 58d of the attitude altering operation piece 58 can be each manipulated by the right hand then gripping the right handle 50R.

Figure 12:
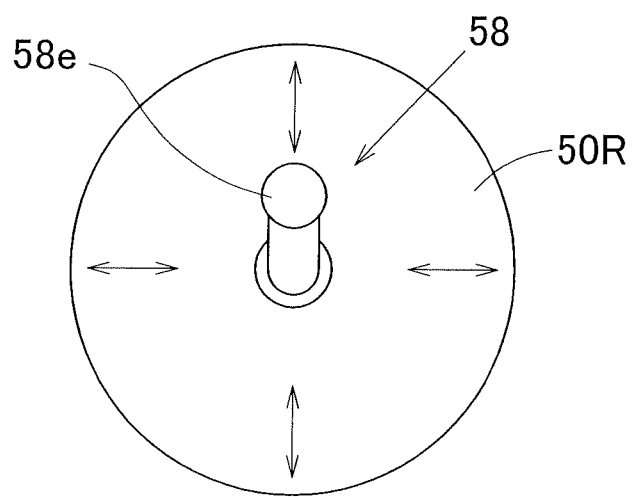
FIG. 12 is a diagram showing a different example of the attitude altering tool.

The attitude altering operation piece 58 may be in the form of a joystick as shown in FIG. 12. The attitude altering operation piece 58, which is in the form of a joystick, includes a lever 58e having a freedom in two directions. When this lever 58e is tilted upwards, the distal end member 2 is tilted upwards; when the lever 58e is tilted downwards, the distal end member 2 is tilted downwards; when the lever 58e is tilted leftwards, the distal end member is tilted leftwards; and when the lever 58e is tilted rightwards, the distal end member 2 is tilted rightwards.

As best shown in FIG. 8, the control box 7 has an outer front surface provided with a display panel 61 of a liquid crystal display type, which is a rotational condition display section and an attitude display section, an initial attitude control indicator lamp 62, an initial attitude operating piece 63 and various operating pieces 64. The initial attitude operating piece 63 and the various operating pieces 64 are employed in the form of, for example, push button switches. Functions of those machine elements will be described in detail later.

Also, as best shown in FIG. 13, a computer 5A used to perform various controls is built in the control box 7. This computer 5A includes a tool rotation control section 71 for controlling the tool rotation drive source 41 and an attitude control section 53 for controlling the attitude control drive source 42 (42U, 42L and 42R).

The tool rotation control section 71 provides an output signal to a motor driver 73 in dependence on a rotation command signal fed from the rotation ON/OFF operating piece 57 to thereby switch the tool rotation drive source 41 on or off. By so doing, the spindle 13 is driven or halted. By way of example, if the rotation ON/OFF operating piece 57 is pushed one time, the spindle 13 is rotated, but when the rotation ON/OFF operating piece 57 is pushed next time, the spindle 13 then rotating is halted. Conditions required for the rotation of the spindle 13 are displayed on the display panel 61 which is the rotational condition display section. One of those conditions includes, for example, whether or not the distal end member 2 is properly fixed.

The attitude control section 53 includes an initial attitude hold control unit 53a and an attitude alteration control unit 53b.

The attitude alteration control unit 53b provides an output signal to a motor driver 74 in dependence on an actuation command signal resulting from an input manipulation of the attitude altering operation piece 58 to thereby drive the attitude control drive source 42 (42U, 42L and 42R). By way of example, the amount of drive of the attitude control drive source 42 is proportional to the operate time of the attitude altering operation piece 58. When depending on which one of the operating pieces 58a, 58b, 58c and 58d is manipulated, the direction of the output and the magnitude of the output for each of the attitude control drive sources 42U, 42L and 42R are changed, the attitude of the distal end member 2 can be altered.

For example, when the operating piece 58*b* is manipulated to provide an output signal, such output signal is provided to each of the attitude control drive sources 42U, 42L and 42R. Then, in a manner similar to that described in connection with the first embodiment of the present invention, the upper attitude altering member 31U shown in FIGS. 2A to 2D is advanced towards the tip end side and the remaining two attitude altering members 31L and 31R are retracted. Once this takes place, the housing 11 for the distal end member 2 is pressed by the upper attitude altering member 31U with the distal end member 2 consequently altered in attitude along the guide faces f1 and f2 so as to permit the tip end side thereof to be oriented downwards. In the event that the operating piece 58*a* is manipulated to provide an output signal, each of the attitude altering members 31 is advanced or retracted in a direction reverse to that described above and the housing 11 for the distal end member 2 is pressed by the left and right attitude altering members 31L and 31R with the distal end member 2 consequently altered in attitude along the guide faces f1 and f2 so as to permit the tip end side to be oriented upwardly.

Also, in the event that the operating piece 58*c* is manipulated to provide an output signal, such output signal is provided to each of the left and right attitude control drive sources 42L and 42R to cause the right attitude altering member 31R to advance towards the tip end side and the left attitude altering member 31L to retract. Then, the housing 11 of the distal end member 2 is pressed by the right attitude altering member 31R and, consequently, the distal end member 2 is altered in attitude so as to be oriented leftwards, that is, towards the side forwardly of the plane of the sheet of FIG. 2A, along the guide faces f1 and f2. On the other hand, in the event that the operating piece 58*d* is manipulated to provide an output signal, the attitude altering members 31L and 31R are advanced or retracted in a manner reverse to those in the case of manipulating the operating piece 58*c* and the housing 11 of the distal end member 2 is therefore pressed by the left attitude altering member 31L, resulting in the attitude of the distal end member 2 altered so as to be oriented rightwards along the guide faces f1 and f2.

Figure 14A:
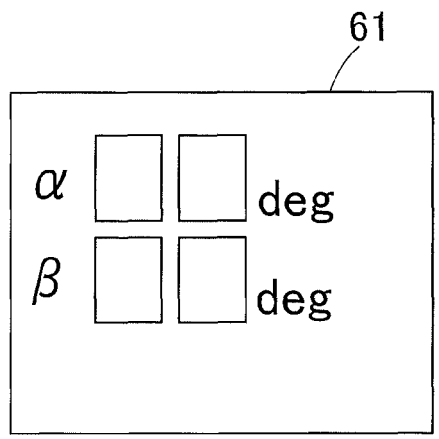
FIG. 14A is a diagram showing a display condition in an indicator employed in the remote controlled actuator.
Figure 14B:
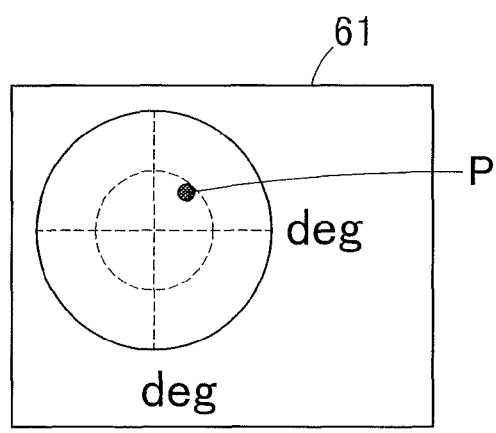
FIG. 14B is a diagram showing a different display condition in the indicator employed in the remote controlled actuator.

The attitude of the distal end member 2 is displayed by the display panel 61 forming the attitude indicating device. Examples of display so effected are shown respectively in FIGS. 14A and 14B. Specifically, FIG. 14A illustrates angles of tilts of the distal end member 2 in the two-axis directions each in terms of a numerical value. By way of example, the legend "a" represents the angle of tilt in the up and down direction (vertical direction) whereas the legend "β" represents the angle of tilt in the leftward and rightward direction (horizontal direction). FIG. 14B illustrates the direction of tilt of the distal end member 2 and the angle of tile of the distal end member 2, which are expressed on the display panel 61 in terms of a point P on the graph. If desired, those two different manners of display appearing on the display panel 61 may be selectively displayed one at a time. In such case, arrangement must be made that a display manner changeover command can be applied to an attitude display control section 75 by means of the various operating pieces 64 shown in FIG. 13 to select one of the manners of display discussed above.

In the condition in which the lock operating piece 49 is depressed one time, the function of the attitude alteration control unit 53*b* is halted. Because of this, even though the attitude altering operation piece 58 is manipulated, the attitude control drive source 42 will not be driven and the distal end member 2 is therefore fixed in a predetermined attitude. However, when the lock operating piece 49 is depressed again, the halt of the function of the attitude alteration control unit 53*b* is released and the attitude of the distal end member 2 can therefore be altered.

In place of the switching between the function halted condition and the halted function release condition of the attitude alteration control unit 53*b*, which is accomplished by means of the lock operating piece 49 as hereinabove described, arrangement may be made that unless the lock operating piece 49 is kept depressed, the manipulation of the attitude altering operation piece 58 is disabled. Conversely, arrangement may be made that only during the period in which the lock operating piece 49 is depressed, the manipulation of the attitude alteration piece 58 is disabled.

Figure 15A:
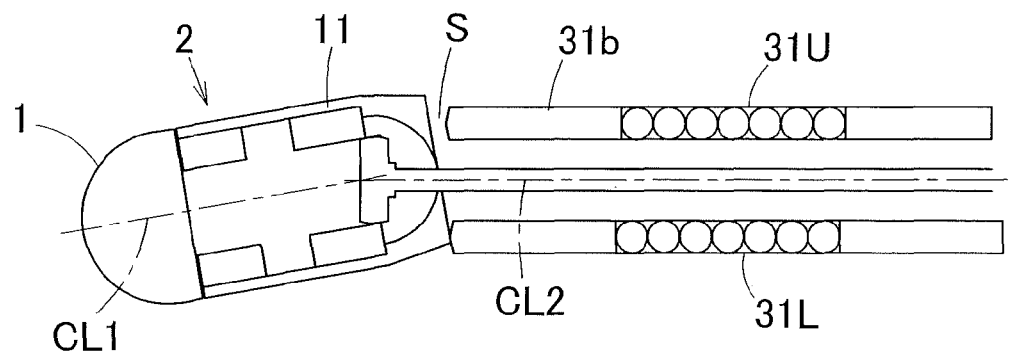
FIG. 15A is an explanatory diagram used to explain an initial attitude control and showing respective conditions of the distal end member and the spindle guide section assumed before the initial attitude control is effected.
Figure 15B:
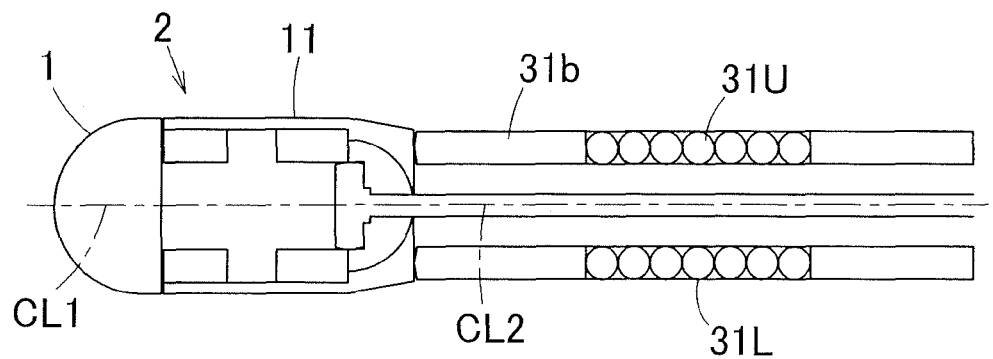
FIG. 15B is an explanatory diagram used to explain the initial attitude control and showing respective conditions of the distal end member and the spindle guide section assumed after the initial attitude control has been effected.

The initial attitude hold control unit 53*a* is operable to control each of the attitude control drive sources 42 so that in a manner similar to that shown and described in connection with the previously described first embodiment of the present invention, the initial attitude holding force F0 (FIG. 5) effective to enable the attitude of the distal end member 2 to be maintained at the arbitrarily preset initial attitude can be applied to the attitude altering member 31. Also, this initial attitude hold control unit 53*a* is operable to perform such a control as to set the distal end member 2 to the initial attitude in response to an activation command signal generated from the initial attitude operating piece 63. Since the initial attitude operating piece 63 is employed and, also, the attitude control section 53 includes the initial attitude hold control unit 53*a*, the initial attitude of the distal end member 2 can be set arbitrarily, the initial attitude can be forcibly resumed manually, and the initial attitude can be accurately restored. For example, immediately after the supply of an electric power to the remote controlled actuator is initiated or at the time of initial manipulation subsequent to replacement of the tool 1, there is the possibility that a gap S may be formed between the base end face of the housing 11 of the distal end member 2 and the pillar shaped pin 31*b* of the attitude altering member 31 as shown in FIG. 15A. For this reason, it is necessary to remove the gap S by allowing the distal end member 2 to resume the initial attitude. The initial attitude is the attitude, in which, for example, the center line CL1 of the distal end member 2 and the center line CL2 of the spindle guide section 3 are concentrically aligned with each other as shown in FIG. 15B. The actuation position of each of the attitude control drive sources 42 during the initial attitude is stored in a storage section 76. It is to be noted that FIGS. 15A and 15B correspond respectively to FIGS. 6 and 5, which pertain to the previously described first embodiment of the present invention.

Figure 16:
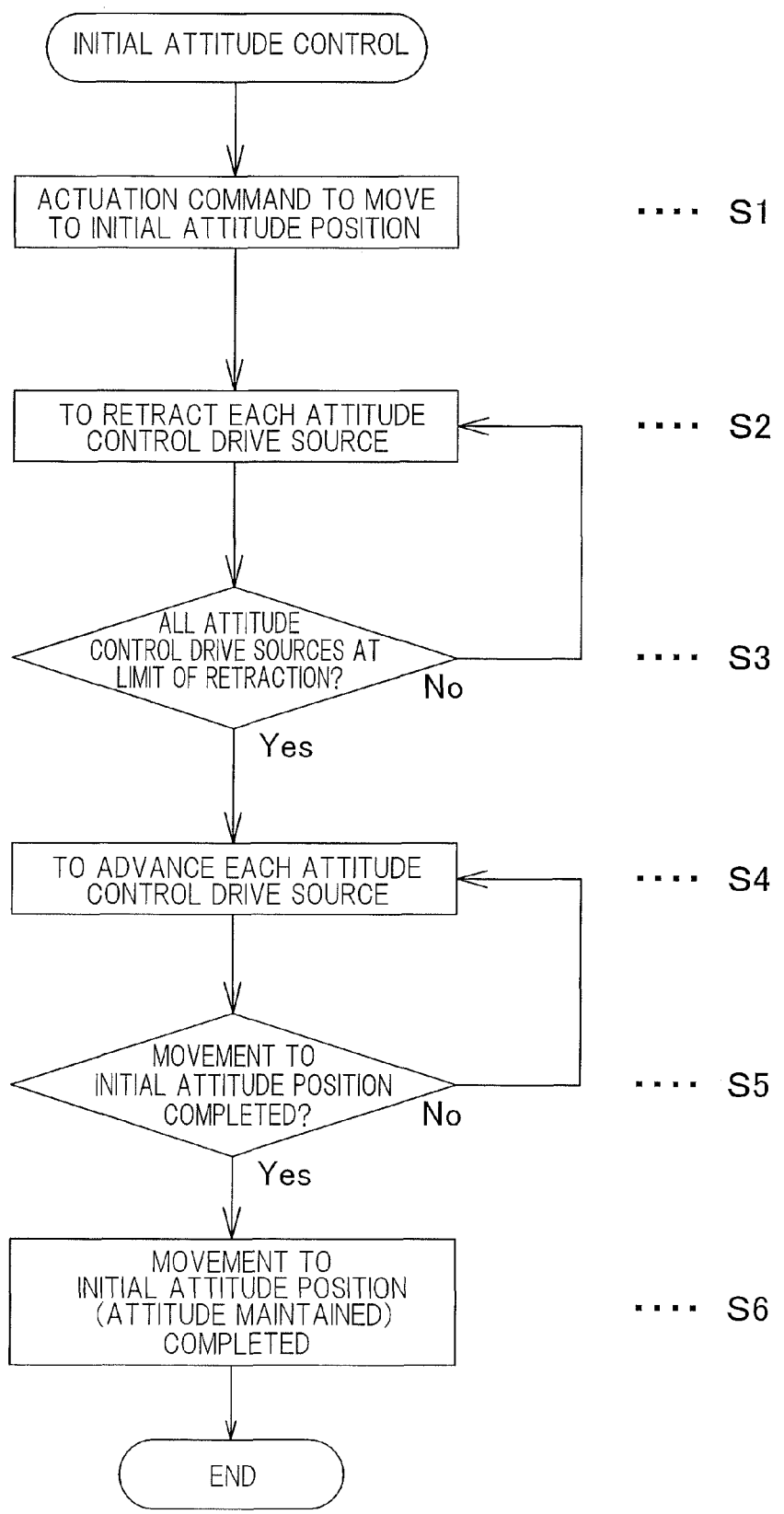
FIG. 16 is a flow chart showing the sequence of the initial attitude control that is effected in the remote controlled actuator.

The initial attitude control is carried out specifically in the sequence as shown in the flowchart of FIG. 16. When the initial attitude operating piece 63 is manipulated and the actuation command to the initial attitude position is received (at step S1), each of the attitude control drive sources 42 is retracted (at step S2). The actuation position of each of the attitude control drive sources 42 is detected by the attitude detector 48. Once all of the attitude control drive sources 42 are retracted to an end of retraction within the range of selective advance and retraction (at step 3), each of the attitude control drive sources 42 is advanced (at step S4). When movement of each of the attitude control drive sources 42 to the arbitrarily preset initial attitude position is completed (at step S5), advance of each of the attitude control drive sources 42 is halted and the movement to the initial attitude position completes (at step S6). Movement of each of the attitude control drive sources 42 to the initial attitude position confirms that the actual actuation position of each of the attitude control drive sources 42 indicated by the output from the attitude detector 48 coincides with the actuation position of each of the attitude control drive sources 42 in the arbitrarily preset initial attitude stored in the storage section 76. The progress of this initial attitude control is step by step displayed by the initial attitude control indicator lamp 62, for example, in such a manner that the indicator lamp 62 is turned off during the uncompleted operation, blinks during the movement towards the initial attitude position, and is turned on upon completion of the movement to the initial attitude position. It is to be noted that the term "uncompleted operation" referred to above means the timing immediately after the remote controlled actuator is electrically powered on, the timing during which subsequent to replacement of the tool 1, the movement towards the initial attitude position is never effected with the use of the initial attitude operating piece 62, and the timing at which during the movement towards the initial attitude position, disagreement between the actuation position of each of the attitude control drive sources 42 detected and the arbitrarily preset initial attitude stored in the storage section 76 occurs.

As hereinbefore described, the remote controlled actuator according to this embodiment is manipulated with the actuator body 6 held by hands then gripping the left and right handles 50L and 50R. With the rotation ON/OFF operating piece 57 manipulated, the spindle 13 is rotated to allow the tool 1 to undergo cutting of the bone. Since the conditions required for the rotation of the spindle 13 are displayed by the display panel 61 serving as the rotational condition display section, the spindle 13 is prevented from being rotated under improper conditions.

During the processing, manipulation of the attitude altering operation piece 58 according to the shape of a processing site and/or the progress of the processing results in change of the attitude of the distal end member 2 in the two-axis directions by remote control. When the lock operating piece 49 is manipulated, the processing can be carried out while the distal end member 2 is maintained in the predetermined attitude. Since the rotation ON/OFF operating piece 57, the attitude altering operation piece 58 and the lock operating piece 49 can be manipulated by hand while the left and right handles 50L and 50R are gripped, the operator can use his or her sensory perception to perform the required manipulation and as a result, the intended work can readily be accomplished. In particular, since the attitude altering operation piece 58 is in the form of a crisscross switch and the operating pieces 58a, 58b, 58c and 58d are so arranged as to coincide with the respective directions in which the attitude is desired to be altered, the operator can feel the actual alteration of the attitude of the distal end member 2 through his or her hands touching any one of the operating pieces 58a, 58b, 58c and 58d and therefore, alteration of the attitude can be accurately and quickly accomplished.

Figure 17A:
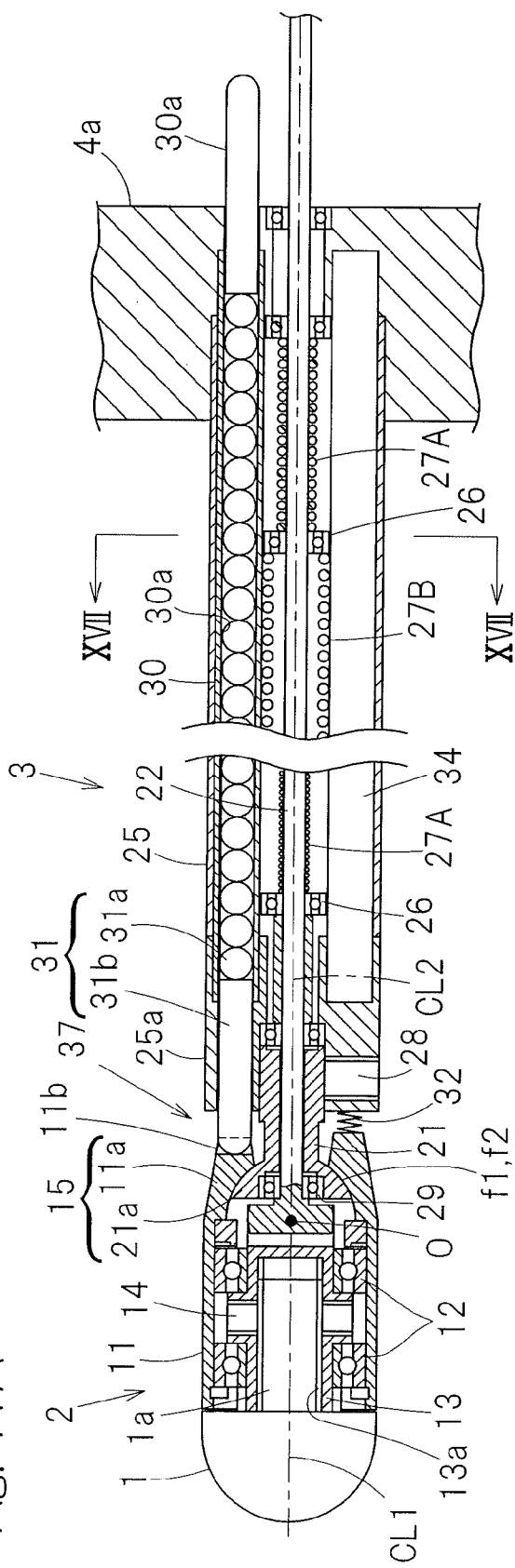
FIG. 17A is a sectional view showing the distal end member and the spindle guide section, both employed in the remote controlled actuator according to a fourth preferred embodiment of the present invention.
Figure 17C:
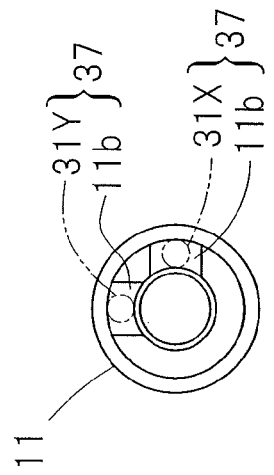
FIG. 17C is a diagram showing the housing for the distal end member as viewed from the base end side thereof.
Figure 17B:
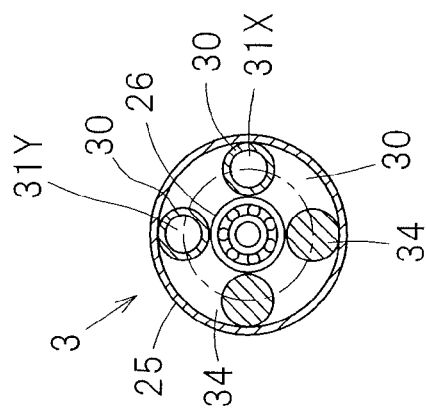
FIG. 17B is a cross sectional view taken along the line XVII-XVII in FIG. 17A.

FIGS. 17A to 17C illustrate the distal end member 2 and the spindle guide section 3 both employed in the remote controlled actuator designed according to a fourth preferred embodiment of the present invention. This remote controlled actuator includes the guide pipe 30 and the attitude altering member 31 each provided at two locations spaced 90° from each other in the circumferential direction. Those two attitude altering members 31X and 31Y are independently and selectively advanced or retracted by two attitude control drive sources (not shown), respectively. At a position spaced 180° in phase in the circumferential direction relative to the circumferential position at which the attitude altering member 31 is located, a restoring elastic member 32 in the form of, for example, a compression coil spring is provided between the base end face of the housing 11 of the distal end member 2 and the distal end face of the outer shell pipe 25 of the spindle guide section 3. This restoring elastic member 32 is operable to bias the distal end member 2 towards a predetermined attitude side.

In the construction described above, when the upper attitude altering member 31Y shown in FIGS. 17A to 17C is advanced towards the tip end side, the housing 11 of the distal end member 2 is pressed by the attitude altering member 31Y and the distal end member 2 is consequently altered in attitude along the guide faces F1 and F2 with the tip end side oriented downwardly as viewed in FIG. 17A. When the attitude altering member 31Y is retracted, the housing 11 of the distal end member 2 is urged to return by the effect of the elastic force of repulsion exerted by the corresponding restoring elastic member 32 and the distal end member 2 is consequently altered in attitude along the guide faces f1 and f2 with its tip end side oriented upwardly as viewed in FIG. 17A. During this attitude altering operation, the pressure of the attitude altering member 31, the elastic force of repulsion exerted by the restoring elastic member 32 and the reactive force from the constraint member 21 act on the distal end member coupling unit 15 and, therefore, the attitude of the distal end member 2 is determined by the effect of the balance of those forces.

Also, when the right attitude altering member 31X shown in FIGS. 17A to 17C is advanced towards the tip end side, the housing 11 of the distal end member 2 is pressed by the attitude altering member 31X and the distal end member 2 is consequently altered in attitude along the guide faces f1 and f2 with the tip end side oriented leftwards. When the attitude altering member 31X is retracted, the housing 11 of the distal end member 2 is urged backwards by the effect of the elastic force of repulsion exerted by the corresponding restoring elastic member 32 and the distal end member 2 is consequently altered in attitude along the guide faces f1 and f2 with its tip end side oriented rightwards. During this attitude altering operation, the pressure of the attitude altering member 31Y, the elastic force of repulsion exerted by the restoring elastic member 32 and the reactive force from the constraint member 21 act on the distal end member coupling unit 15 and, therefore, the attitude of the distal end member 2 is determined by the effect of the balance of those forces.

As described above, even when the attitude altering members 31X and 31Y and the restoring elastic member 32 are concurrently utilized, the attitude of the distal end member 2 can be altered in the two-axis directions. Even in such case, the attitude altering drive mechanism (not shown) and the attitude control section (also not shown) are of respective structures identical with those described previously.

While in each of the foregoing embodiments of the present invention, the spindle guide section 3 is of a rectilinear shape, the remote controlled actuator of the present invention is such that even when the attitude altering member 31 has a flexibility and the spindle guide section is curved, the attitude altering operation of the distal end member 2 can be performed assuredly. Therefore, the spindle guide section 3 may have a curved shape in its initial state. Alternatively, only a portion of the spindle guide section 3 may have a curved shape. If the spindle guide section has a curved shape, it may occur that the distal end member 2 can be inserted deep into the bone where the spindle guide section of the rectilinear shape fails to reach and, hence, the processing to form the artificial joint insertion hole during the artificial joint replacement surgery can be finished accurately.

While the various preferred embodiments of the present invention have been fully described hereinabove, the following mode is available, which does not require the use of the initial attitude hold control unit 53a of the present invention:

[Mode]

The remote controlled actuator according to this mode includes an elongated spindle guide section, a distal end member fitted to a distal end of the spindle guide section through a distal end member coupling unit for alternation in attitude, and a drive unit housing coupled with a base end of the spindle guide section and capable of being held by hand;

in which the distal end member rotatably supports a spindle for holding a tool, in which the spindle guide section includes a rotary shaft for transmitting rotation of a tool rotation drive source, provided within the drive unit housing, to the spindle, and a guide hole defined therein so as to extend from one end to the opposite end, in which an attitude altering member for altering the attitude of the distal end member as a result of advancing or retracting operation with its tip end held in contact with the distal end member is reciprocally movably inserted within the guide hole, in which an attitude control drive source for selectively advancing and retracting the attitude altering member is provided within the drive unit housing, and an attitude altering operation piece for changing the attitude of the distal end member by issuing an actuation command signal directly or indirectly to the attitude control drive source in response to an input manipulation is provided outside the drive source housing, and in which the attitude altering operation piece is capable of being manipulated by hands then holding the drive source housing.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1: Tool
2: Distal end member
3: Spindle guide section
4a: Drive unit housing
5: Controller
5A: Computer
6: Actuator body
7: Control box
13: Spindle
15: Distal end member coupling unit
22: Rotary shaft
25: Outer shell pipe
30: Guide pipe
30a: Guide hole
31: Attitude altering member
34: Reinforcement shaft
41: Tool rotation drive source
42: Attitude control drive source
43: Force increasing and transmitting mechanism
45: Reverse input preventing mechanism
46: Actuation amount detector
47: Strain sensor
48: Attitude detector
49: Lock operating piece
50L, 50R: Handle
51: Attitude setting device
53: Attitude control section
53a: Initial attitude hold control unit
53b: Attitude alteration control unit
54: External force estimating section
57: Rotation ON/OFF operating piece
58: Attitude altering operation piece
61: Display panel (Rotational condition display section, Attitude display section)
63: Initial attitude operating piece
71: Tool rotation control section
76: Storage section

What is claimed is:

1. A remote controlled actuator, which comprises:
a spindle guide section of an elongated shape, a distal end member fitted to a distal end of the spindle guide section through a distal end member coupling unit for alteration in attitude, and a drive unit housing coupled with a base end of the spindle guide section;
wherein the distal end member rotatably supports a spindle for holding a tool,
wherein the spindle guide section includes a rotary shaft for transmitting rotation of a tool rotation drive source, provided within the drive unit housing, to the spindle and a guide hole defined therein so as to extend from one end to the opposite end,
wherein an attitude altering member having a tip end held in contact with the distal end member is reciprocally movably inserted within the guide hole,
wherein an attitude control drive source for applying to the attitude altering member a force acting in a direction of advance and retraction is provided within the drive source housing and, also, an attitude control section for controlling the attitude control drive source is provided, and
wherein the attitude control section includes an initial attitude hold control unit for controlling the attitude control drive source to apply to the attitude altering member an initial attitude holding force necessary to enable the attitude of the distal end member to hold in an arbitrarily preset initial attitude, and an attitude alteration control unit for controlling the attitude control drive source to apply to the attitude altering member a force greater than the initial attitude holding force being applied to the attitude altering member so that the attitude of the distal end member is altered by selectively advancing or retracting the attitude altering member.

2. The remote controlled actuator as claimed in claim 1, in which the attitude of the distal end member is determined in dependence on an amount of reciprocal movement of the attitude altering member relative to a reference position, which is defined as a position of the attitude altering member assumed when the distal end member is in the initial attitude.

3. The remote controlled actuator as claimed in claim 2, further comprising an attitude setting device for setting a target attitude of the distal end member,
wherein the attitude alteration control unit is operable to convert the target attitude of the distal end member, preset by the attitude setting device, into an amount of advance or retraction of the attitude altering member, which corresponds thereto, and to change an amount of actuation of the attitude control drive source in dependence on the amount of advance or retraction so converted.

4. The remote controlled actuator as claimed in claim 3, further comprising an actuation amount detector for detecting the amount of actuation of the attitude control drive source and feeding an output thereof back to the attitude alteration control unit.

5. The remote controlled actuator as claimed in claim 1, further comprising a reverse input preventing mechanism for preventing the attitude control drive source from actuating by the effect of a force from the distal end member, which mechanism is provided in the attitude control drive source or between the attitude control drive source and the distal end member.

6. The remote controlled actuator as claimed in claim 1, in which the attitude control drive source is an electrically driven actuator, the electrically driven actuator being driven by an electric power of PWM wave.

7. The remote controlled actuator as claimed in claim 1, in which the attitude control drive source is a linear actuator and further comprising a force increasing and transmitting mechanism for increasing a thrust force of the linear actuator and then transmitting it to the attitude altering member, the force increasing and transmitting mechanism being comprised of a lever mechanism.

8. The remote controlled actuator as claimed in claim 7, further comprising a strain sensor for detecting a strain occurring in the lever of the force increasing and transmitting mechanism, and an external force estimating section for estimating an external force, acting on the distal end member, in reference to an output of the strain sensor.

* * * * *